(12) United States Patent
Li

(10) Patent No.: US 7,935,816 B2
(45) Date of Patent: May 3, 2011

(54) MOLECULAR TRANSPORTER COMPOSITIONS COMPRISING DENDRIMERIC OLIGOGUANIDINE WITH A TRIAZINE CORE THAT FACILITATE DELIVERY INTO CELLS IN VIVO

(75) Inventor: Yong-Fu Li, Corvallis, OR (US)

(73) Assignee: Gene Tools, LLC, Philomath, OR (US)

( * ) Notice: Subject to any disclaimer, the term of this patent is extended or adjusted under 35 U.S.C. 154(b) by 371 days.

(21) Appl. No.: 11/977,800

(22) Filed: Oct. 25, 2007

(65) Prior Publication Data
US 2009/0171075 A1    Jul. 2, 2009

(51) Int. Cl.
*A61K 47/48*    (2006.01)
*C07D 403/04*   (2006.01)
*C07H 21/00*    (2006.01)

(52) U.S. Cl. ........................ 544/198; 536/23.1
(58) Field of Classification Search ................ None
See application file for complete search history.

(56) References Cited

U.S. PATENT DOCUMENTS
7,084,248 B2   8/2006  Summerton
2003/0032593 A1   2/2003  Wender et al.

FOREIGN PATENT DOCUMENTS
WO   WO91/09958   7/1991
WO   WO94/04686   3/1994

OTHER PUBLICATIONS

Chung (Feb. 11, 2004) Biopolymers Peptide Science vol. 76 pp. 83 to 96.*
Gaelle DeGlane et al,"Impact of the Guanindinium Group on Hybridization..",ChemBioChem 2006, 7, 684-692, Wiley-VCH Verlag Gmbh&Co. KGaA, Weinheim.
Shin-Hong Kang et al,"Up-Regulation of Luciferase Gene Expression with Antisense Oligonucleotides: . . . ",Biochemistry 1998,37,6235-6239, Web Publication Apr. 14, 1998.
Peter Sazani,"Systemically Delivered Antisense Oligomers Upregulate Gene Expression in Mouse Tissues," Nature Biotechnology, vol. 20, Dec. 2002, Web Publication Nov. 11, 2002.
Michael S. Bernatowicz et al, "H-Pyrazole-1-carboxamidine Hydrochloride: An Attractive Reagent for Guanylation of Amines . . . ", American Chemical Society, 1992, 57, 2497-2502.
Kui Huang,"Dendritic Molecular Transporters Provide Control of Delivery to Intracellular Compartments," Bioconjugate Chem, 2007, 18, 403-409, Web Publication Feb. 7, 2007.
Jonathan B. Rothbard et al,"Role of Membrane Potential and Hydrogen Bonding in the Mechanism of Translocation . . . ,"J.Am.Chem. Soc. 2004,126,9506-9507.
Paul A. Wender,"Dendrimeric Molecular Transporters: Systhesis and Evaluation . . . ",Am.Chem.Soc. 2005,Web Publication Sep. 27, 2005.

(Continued)

*Primary Examiner* — Jeffrey S. Lundgren
*Assistant Examiner* — Christian Boesen
(74) *Attorney, Agent, or Firm* — Teri G. Andrews Attorney at Law

(57) ABSTRACT

Preparations of novel molecular transporter compositions and their use for transporting bioactive substances into cells in living animals are disclosed. To afford in vivo delivery, the composition is covalently linked to the bioactive substance and the resultant composite structure is introduced into the subject. The transporter composition includes multiple guanidine moieties on a dendrimeric scaffold having a triazine core.

7 Claims, 19 Drawing Sheets

OTHER PUBLICATIONS

Hyun-Ho Chung et al,"Dendritic Oligoguanidines as Intracellular Translocators",Wiley Periodicals, Inc. Biopolymers (Pept Sci) 76:83-96,2004.

Shiroh Futaki et al,"Translocation of Branched-Chain Arginine Peptides through Cell Membranes: . . . ",Biochemistry 2002,41,7925-7930.

* cited by examiner

Cells in 10% Serum (24 hours)

Luciferase Activity

| | |
|---|---|
| Control | 11.65 |
| 5 uM EP | 1421.91 |
| 2 uM VM | 49.44 |
| 5 uM VM | 196.50 |
| 10 μM VM | 622.22 |
| 50 uM VM | 986.80 |

Protein Concentration

| | |
|---|---|
| Control | 0.327 |
| 5 uM EP | 0.300 |
| 2 uM VM | 0.261 |
| 5 uM VM | 0.201 |
| 10 uM VM | 0.165 |
| 50 uM VM | 0.123 |

Normalized Light Output

| | |
|---|---|
| Control | 3.82 |
| 5 uM EP | 425.85 |
| 2 uM VM | 12.91 |
| 5 uM VM | 39.39 |
| 10 uM VM | 102.75 |
| 50 uM VM | 120.45 |

Assessment of Vivo-Morpholino (VM) delivery in cultured HeLa Cells grown in 10% serum in comparison with Control (bare Morpholino) and EP (bare Morpholino with Endo-Porter)

Cells in 100% Serum

Luciferase Activity

| | 24 h | 48 h |
|---|---|---|
| Control | 8.20 | 12.02 |
| 5 uM EP | 21.86 | 17.67 |
| 2 uM VM | 13.27 | 15.84 |
| 5 uM VM | 38.01 | 63.05 |
| 10 uM VM | 175.76 | 264.25 |
| 50 uM VM | 444.46 | 652.81 |

Light Unit

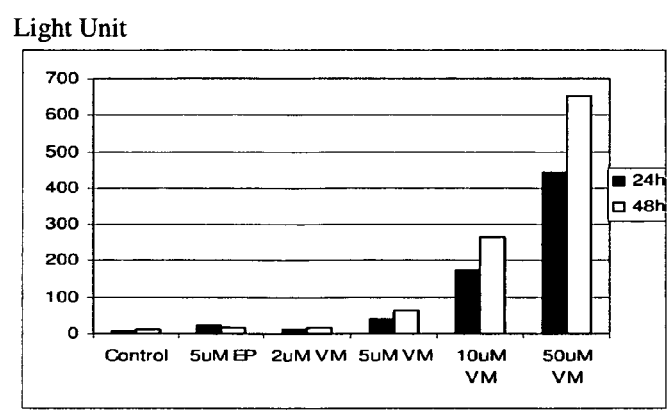

Protein Concentration

| | 24 h | 48 h |
|---|---|---|
| Control | 0.141 | 0.228 |
| 5 uM EP | 0.151 | 0.227 |
| 2 uM VM | 0.153 | 0.219 |
| 5 uM VM | 0.150 | 0.239 |
| 10 uM VM | 0.128 | 0.189 |
| 50 uM VM | 0.086 | 0.100 |

Protein Concentration ($OD_{525}$)

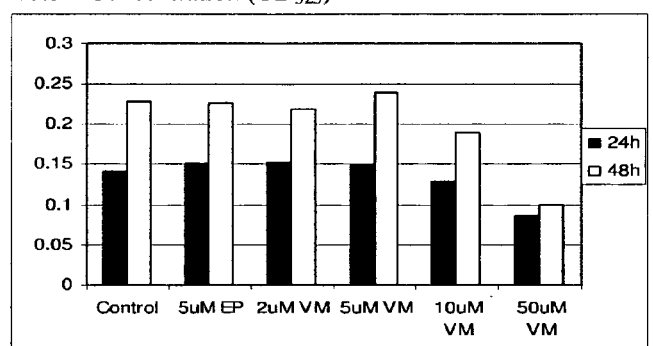

Normalized Light Output

| | 24 h | 48 h |
|---|---|---|
| Control | 1.15 | 2.73 |
| 5 uM EP | 3.28 | 3.93 |
| 2 uM VM | 2.02 | 3.44 |
| 5 uM VM | 5.72 | 15.07 |
| 10 uM VM | 22.36 | 49.63 |
| 50 uM VM | 37.96 | 62.73 |

Light Unit

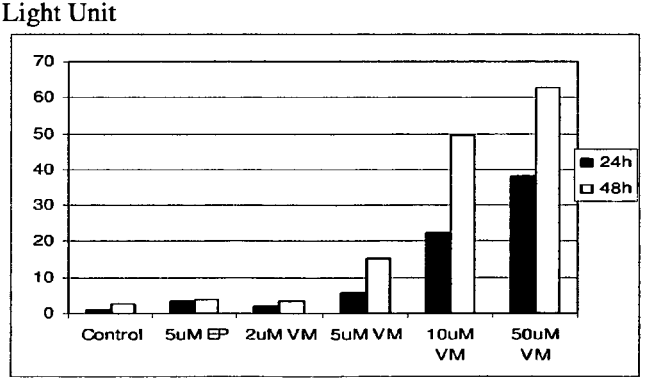

Assessment of Vivo-Morpholino (VM) delivery in cultured HeLa Cells grown in 100% serum in comparison with Control (bare Morpholino) and EP (bare Morpholino with Endo-Porter)

Figure 11

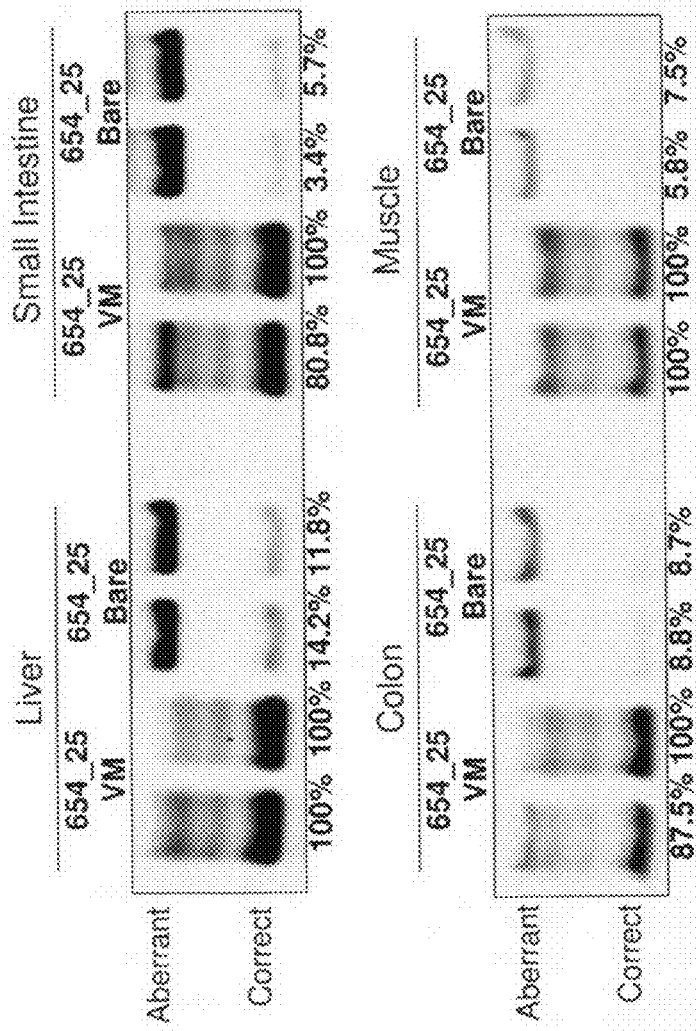

Figure 12a

RT-PCR analysis of splice correction by Vivo-Morpholino (VM) in comparison with bare Morpholino (bare). 654-25 is the Morpholino oligo to correct the splicing defect in transgenic mice. The upper band (Aberrant) results from an unaltered transcript whereas the lower band (Correct) is the RT-PCR product of the shorter corrected transcript. Each lane represents individual mice (n = 2 per group).

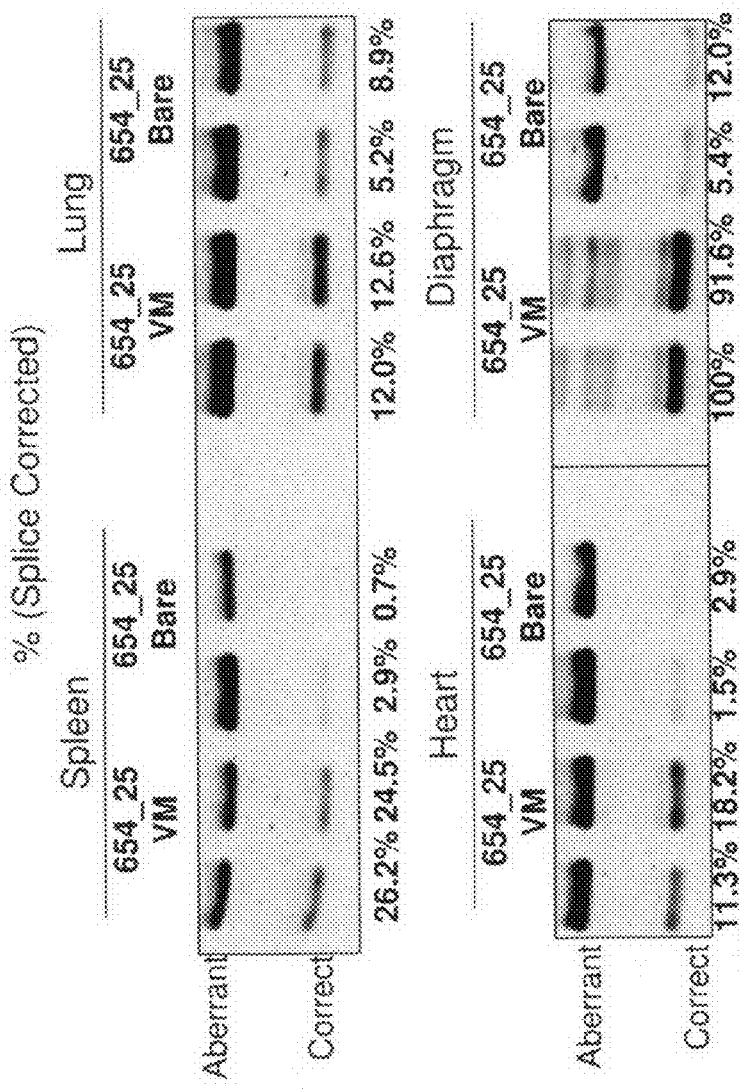

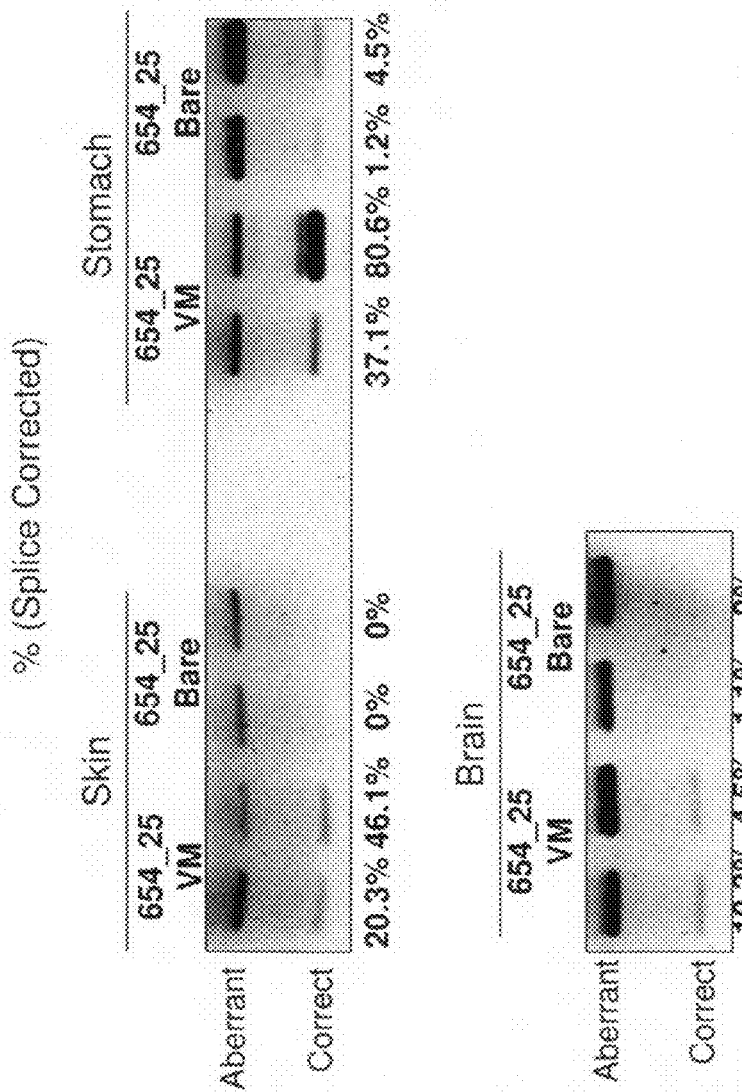

Figure 12c

RT-PCR analysis of splice correction by Vivo-Morpholino (VM) in comparison with bare Morpholino (bare). 654-25 is the Morpholino oligo to correct the splicing defect in transgenic mice. The upper band (Aberrant) results from an unaltered transcript whereas the lower band (Correct) is the RT-PCR product of the shorter corrected transcript. Each lane represents individual mice (n = 2 per group).

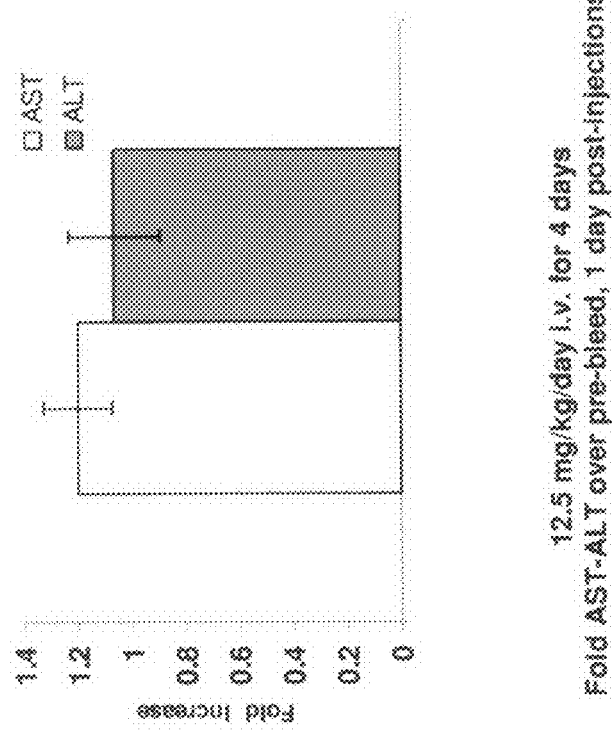

MOLECULAR TRANSPORTER COMPOSITIONS COMPRISING DENDRIMERIC OLIGOGUANIDINE WITH A TRIAZINE CORE THAT FACILITATE DELIVERY INTO CELLS IN VIVO

FIELD OF THE INVENTION

The invention relates to the preparation and use of triazine dendrimeric oligoguanidine effective for transporting bioactive substances into the cytosol of cells in vivo. The compositions contain guanidinium headgroups assembled around a triazine core.

BACKGROUND OF THE INVENTION

While considerable structural diversity is found among drugs and probe molecules which act on intracellular targets, the physical properties of most of these agents are restricted to a narrow range to ensure passage through the polar extracellular milieu and the non-polar lipid bilayer of the cell. This can be problematic in the field of drug discovery where the bioactive substances are impermeable or poorly permeable to the cells in animals. Cellular membranes are particularly impermeable to highly charged compounds such as polynucleotides, or neutral antisense macromolecules, such as Morpholino oligos and peptide nucleic acids. When a high molecular weight bioactive molecule (e.g. Morpholino oligo) is administered to an organism, its medicinal utility is generally limited by its inability to efficiently gain access to its intracellular target.

Researchers have attempted to develop technologies for enhancing the transport of chemical compounds across organismal barriers. For instance, Frankel et al. report the conjugation of selected molecules to HIV TAT protein (Frankel et al., PCT Pub. No. WO 91/09958 (1991)). Barsoum discusses the use of the HIV TAT peptide sequence RKKRRQRRR for enhancing transport across cellular membranes (Barsoum et al., PCT Pub. No. WO 94/04686 (1994)). Wender et al. discuss the use of oligoarginine moieties for increasing the delivery of various molecules across cellular membranes (Wender et al., US2003/0032593).

The enormous potential of arginine-based molecular transporters has stimulated efforts to develop improved structures for delivery of large polar molecules into cells. However, researchers have concluded from a large number of molecular transporters containing arginines in peptide or peptoid assembly, or guanidines in a variety of backbones, that (a) the guanidine headgroups are principally responsible for its uptake into cells, (b) backbone chirality is not critical for cellular uptake, and (c) the number of guanidine head groups between 7 and 15 is optimal for efficient uptake (Rothbard, J. B., et al. *J. Am. Chem. Soc.* 126:9506-9597 (2004)). Therefore, methods and compositions have been described for transporting drugs and macromolecules across biological membranes in which the drug or macromolecule is covalently attached to a transport polymer consisting of a scaffold containing oligoguanidines.

However, the practical application of such oligoguanidine transporters is generally limited due to their high cost and difficulty of use. Usually these oligoguanidines are prepared using a solid-phase synthesizer. Although this approach is readily automated and allows for the synthesis and purification of long oligomers, it suffers drawbacks including high cost, limited scalability, and the need for resin attachment and cleavage. In contrast, solution phase synthesis could avoid the cost and scale restrictions of resins. Despite numerous reports about the importance of guanidine groups in the peptidic backbone of oligoguanidines, most oligoguanidine delivery moieties have a linear structure, while relatively few attempts have been made using guanidine groups in branched architectures. In one such rare case, polyguanidino dendrimers using triamine-based diamino acid monomeric units were synthesized and their delivery efficacy out-performed an oligoarginine reference standard (Wender, P. A., et al. *Organic Letters* 7:4815-4818 (2005)). Branched-chain arginine peptides also have the ability to translocate through cell membranes and to bring exogenous proteins into cells (Futaki, S., et al. *Biochemistry* 41:7925-7930 (2002)). Dendrimeric oligoguanidines based on amino triol subunits are capable of translocation through the cell membrane (Chung, H.-H., et al. *Biopolymers* (Pept. Sci) 76:83-96 (2004)). An alternative architecture based on amino triacid scaffold demonstrated that the dendrimeric molecular transporters can not only enable transport of bioactive cargo across the cell membrane, but also control the delivery into defined intracellular compartments (Huang, K., et al. *Bioconjugate Chem.* 18: 403-409 (2007)).

However, the syntheses of the dendrimeric oligoguanidines mentioned above are lengthy or involve expensive reagents for their assembly. A need clearly exists for new compositions and methods offering superior performance in transporting compounds across biological barriers, as well as being more cost-effective to make and to link to their bioactive substances to be transported into cells. The present invention fulfills these and other needs.

SUMMARY OF THE INVENTION

Dendrimers represent an attractive transporter scaffold that offers the advantages of economical assembly of oligoguanidine transporters through a variant of a segment-multiplying strategy. Triazine, a tri-functional entity, possesses an orthogonal core in which two sites can be used for branching side arms (or side chains) while a bioactive substance can be attached to its third functional site (or a trunk, a linking group for conjugation). Specifically, each arm of a two-arm dendrimer core can be extended with a two-arm segment to give a four-arm first generation product. Repetition of this cycle then leads to an eight-arm system capable of incorporating eight guanidine groups. Therefore, dendrimeric assembly is one of the most efficient ways to construct a molecule containing multiple head groups, which in this specific case, will be guanidine entities. Moreover, since triazine architecture is strange in the living system, some problems such as antigenicity and toxicity, which many peptide-based molecular transporters suffer from, may be avoided, and therefore bioavailability, stability and safety for use in vivo may be improved.

One aspect of the invention relates to a method for the preparation of a scaffold by using triazine as its core structure. One site on this triple functional core provides for linking covalently to a bioactive substance via a leash or a lining group which can be either permanent or cleavable by biological means, such as proteases, lipase or reductases, or by other means such as photolysis. The other two functional sites of the core are used for anchoring the dendrimeric arms.

Another aspect of the invention pertains to a method for the preparation of an oligoguanidine compound, comprising the steps of: (a) contacting an oligomer having a plurality of chemically tethered amines, wherein a portion of the tethered amines have attached protecting groups, with a protecting group removal agent to remove each of the protecting groups to produce an oligomer having a plurality of chemically tethered amines; and (b) contacting said oligomer having a plurality, of chemically tethered amines with a guanidinylation reagent to convert each of said chemically tethered amines to a guanidinyl group to produce an oligoguanidine compound.

Yet another aspect of the invention relates to the process where the chemically tethered amines generated from removal of protecting groups are used directly for converting to guanidine by a specific composition containing a certain concentration of ammonia and a selected guanidinylation reagent, and by selected reaction conditions including a selected range of reaction time and reaction temperature.

Yet another aspect of the invention relates to the synthetic scheme where the protected scaffold is attached to a bioactive substance in protected form. Removal of the protecting groups to generate the chemically tethered amines, followed by addition of a guanidinylation reagent to convert each of said chemically tethered amines to a guanidinyl group produces a conjugate containing the transporter composition and a bioactive substance.

Yet another aspect of the invention relates to the compositions comprising oligoguanidine delivery moiety covalently linked to substantially non-ionic antisense oligos. The conjugate of the transporter composition of this invention with Morpholino antisense oligo has been administered intravenously into transgenic mice. Functional quantitative assessment of intracellular delivery indicates that unprecedented levels of delivery have been achieved in tissues such as liver, small intestine, colon, muscle and diaphragm. Although less effective than the intravenous administration, intraperitoneal administration can also be used as a means to deliver the conjugate of the transporter composition of this invention and a bioactive substance into animals, including humans.

Yet another aspect of the invention relates to the use of said compositions for modifying gene expression in living subjects. Morpholinos have been shown to be effective to block translation, to alter mRNA splicing and to block binding of regulatory proteins to RNA. Splicing-blocking morpholinos can delete exons and facilitate the study of specific spliceforms of a gene with multiple splice variants. A morpholino oligo conjugated with the transporter composition of this invention works effectively in vivo to block translation of a selected mRNA and to modify splicing of a selected pre-mRNA.

BRIEF DESCRIPTION OF THE DRAWINGS

FIG. 11 illustrates the functional efficacy assay of delivering Morpholino conjugated with the transporter composition in 100% serum cell culture in comparison with the Morpholino in the presence of Endo Porter, an amphiphilic transporter peptide.

FIG. 12 illustrates the functional efficacy assay of intravenously delivering Morpholino conjugated with the transporter composition to a variety of organs in live mice.

FIG. 13 illustrates AST-ALT data for implication of toxicity profile in mice for intravenous treatment of a conjugate of transporter composition and Morpholino.

DETAILED DESCRIPTION OF THE INVENTION

I. Abbreviation and Definitions

Figure 1A:
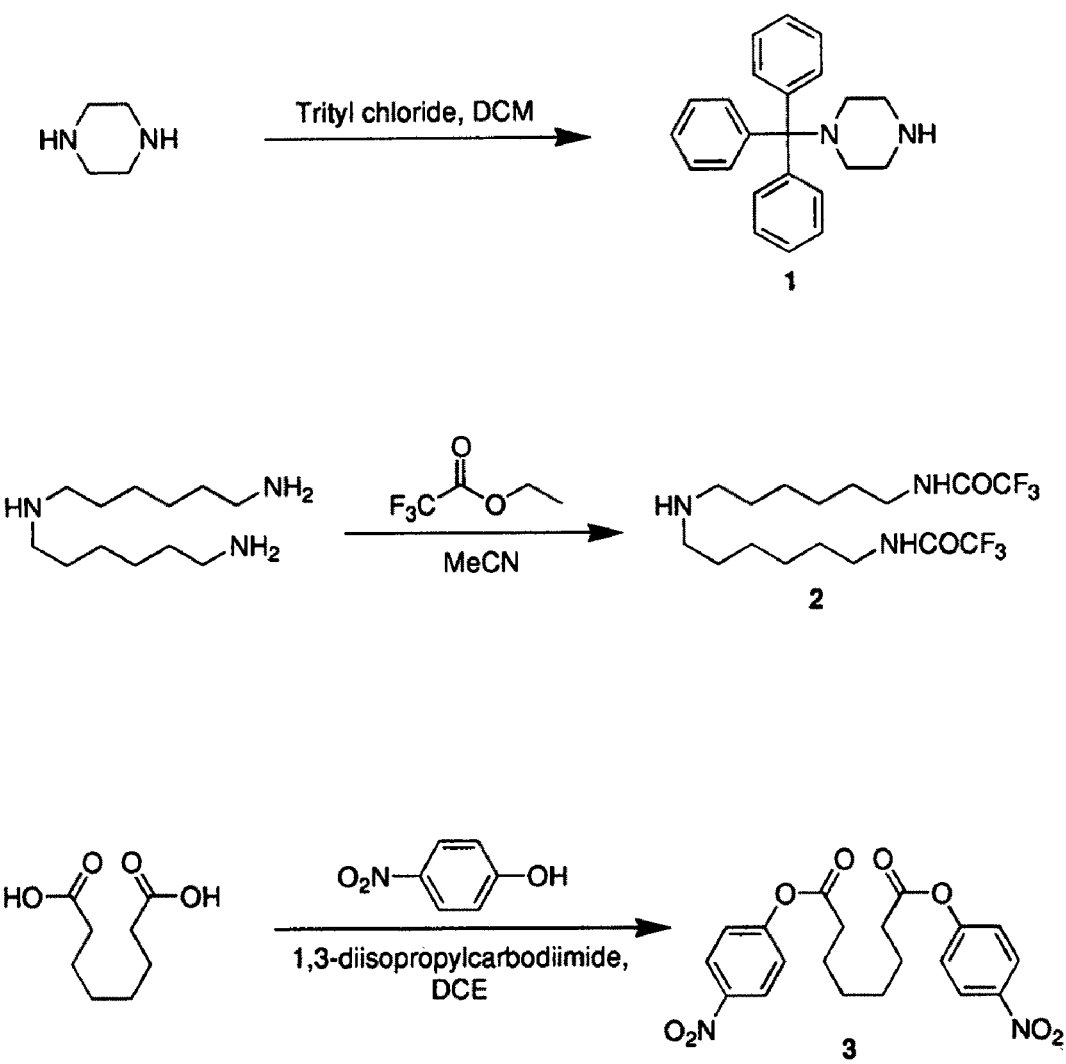
FIG. 1 illustrates a representative synthetic scheme for assembling an octaguanidine of the invention. (a): The synthetic components are prepared from readily available starting materials. (b-d): The assembly starts from cyanuric chloride. The first chloride is substituted by a nitrogen moiety used at a later stage for adding a linking group for conjugating with a bioactive substance. The other two chlorides are substituted by dialcoholamine, doubling the functional groups to tetra-alcohol. Activation of the tetra-alcohol to reactive carbonate, followed by introduction of secondary amine entities each containing two suitably protected primary amino groups, gives a triazine core scaffold containing a central nitrogen in protected form and eight side chains each with a protected primary amino group. After removal of the protecting group of the central nitrogen, a linking group is installed, the other end of which reacts to conjugate with a bioactive substance. Removal of the protecting groups for the side chains, followed by guanidinylation, gives a conjugate of transporter composition and bioactive substance. (e): Morpholino as a representative bioactive substance is shown in a conjugate with the transporter composition.

Before describing detailed embodiments of the invention, it will be useful to set forth abbreviations and definitions that are used in describing the invention. The definitions set forth apply only to the terms as they are used in this patent. The following description of the preferred embodiments and examples are provided by way of explanation and illustration. As such, they are not to be viewed as limiting the scope of the invention as defined by the claims. Additionally, when examples are given, they are intended to be exemplary only and not to be restrictive. For example, when an example is said to "include" a specific feature, that is intended to imply that it may have that feature but not that such examples are limited to those that include that feature.

In describing and claiming the present invention, the following terminology will be used in accordance with the definitions set out below.

"Oligoguanidine compound" refers to an oligomer of subunits, each subunit of which contains a chemically tethered guanidine group. A guanidine residue has the general structural characteristics of a guanidine head group, plus a tether of up to 12 methylene groups linking the guanidine moiety to the core of the transporter composition, where the core includes at least one triazine ring. Accordingly, in one embodiment of the invention, one component of an oligoguanidine compound has the following sectional formula A:

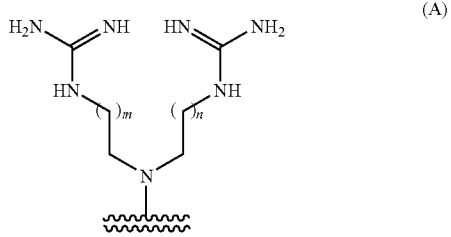

(A)

wherein: m and n are integers of from 2 to 6. In the formula above, the guanidine group is illustrated as being neutral. One of skill in the art will appreciate that the extent to which an oligoguanidine compound is charged will depend on the environment in which it is present (including medium, pH, etc.) and both charged and uncharged forms are contemplated by the present invention.

The core of the oligoguanidine transporter composition is a "triazine" which serves as the scaffold on which the guanidine-containing components are assembled. One site on this triazine moiety is used to install a linker or a linking group for conjugation with bioactive substances. The other two sites on the triazine are used to install the side chains of amino groups in a protected form, which are subsequently deprotected and converted to guanidines, preferably after coupling with bioactive substances. Accordingly, in one embodiment of the invention, the core structure of the delivery composition has the following formula B:

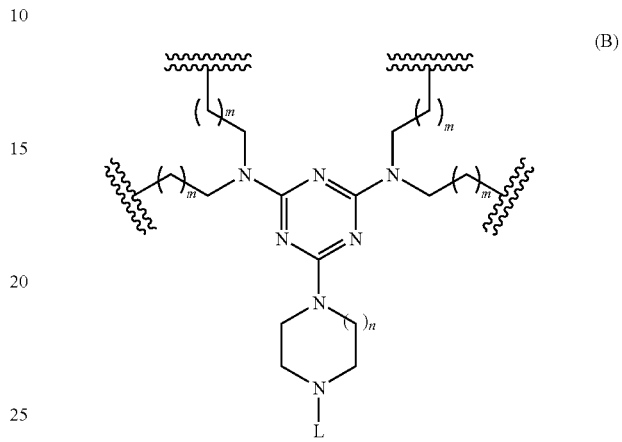

(B)

Wherein: m is an integer of from 0 to 10; n is an integer of from 1 to 5. L is a linker or a linking group to conjugate to a bioactive substance. Therefore, merger of Formula A and B represents a whole piece of transporter composition containing oligoguanidine head groups, triazine core scaffold and a linker bound to or suitable for binding to a bioactive substance.

As used herein, the term "oligoguanidine compound" refers to an oligomer of subunits, each of which contains a chemically tethered group that is a guanidine or that has been chemically transformed to generate a guanidine group. Transformation to the guanidine group can be done prior to the conjugation with a bioactive substance by using an appropriate starting material (i.e., an oligomer having chemically built-in guanidine in a suitably protected form). Alternately, an oligoguanidine compound can be made at the end of the synthesis by a perguanidinylation step.

A linking moiety "L" has two termini, one that covalently attaches to the transporter composition and one that covalently bonds to a bioactive substance. Examples of such groups include, without limitation, carboxylic acid, carboxylic acid derivatives, alcohols, amines and thiols. For example, one end of a dicarboxylic acid is used in attaching the transporter composition, while the other in attaching a bioactive substance. The cleavable linking moiety is preferable when it is used in vivo. "Cleavable" in this case refers to separation of transporter composition from the bioactive substance. The separation is effected through cleavage of a covalent bond unstable in a biological environment. For example, a linking moiety containing a disulfide bond may be cleaved in the reducing environment within cells in the living organism. Or a linking moiety contains a short section of peptide, which can be cleaved by peptidases or proteases in the living organism. The cleavage releases a free bioactive substance from the transporter composition.

"Delivery" refers to an increase in amount and/or rate of transporting a bioactive substance across a biological barrier. The term is also meant to include altering tissue distribution, localization and release of a bioactive substance or agent. "Biological barrier" refers to a physiological barrier to the delivery of a bioactive substance to its intended target site. It includes, for example biological membranes. "Biological membrane" refers to a lipid-containing barrier that separates cells or groups of cells from extracellular space.

"Bioactive substance" refers to a therapeutic compound or a diagnostic agent, as well as lead compounds in a research and development setting. Still further the term is meant to include various probes (e.g., oligonucleotides alone or those having attached imaging agents) and substances effective to alter biological processes within cells.

The term "therapeutic compound" refers, without limitation, to any composition that can be used to the benefit of a mammalian species. A number of such agents cause an observable change in the structure, function or composition of a cell upon uptake by the cell. Observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased rate of synthesis of a metabolite, increased or decreased cell proliferation and the like. Other agents exert therapeutic effects when present in a tissue, even in the absence of cellular entry.

The term "diagnostic agent" refers to both diagnostic imaging agents and contrast agents. The following are non-limiting examples of diagnostic agents: radio-labeled substances such as $^{99m}$Tc glucoheptonate; substances used in magnetic resonance imaging such as gadolinium doped chelation agents (e.g., Gd-DTPA); metals bound to chelating agents such as Eu, Lu, Pr, Gd, Tc$^{99}$m, Ga$^{67}$, In$^{111}$, Y$^{90}$, Cu$^{67}$ and Co$^{57}$; and, proteins such as β-galactosidase, green fluorescent protein and luciferase. Other diagnostic agents include molecular sensors.

The term "macromolecule" refers to large molecules (MW greater than 1000 daltons) of biological or synthetic origin, exemplified by, but not limited to, peptides, proteins, oligonucleotides, polynucleotides and analogs thereof, such as peptide nucleic acids and morpholinos.

"Small organic molecule" refers to a carbon-containing agent having a molecular weight of less than or equal to 1000 daltons.

Abbreviations:
In describing and claiming the present invention, the following abbreviations will be used in accordance with the definitions set out below.
ALT Alanine aminotransferase
AST Aspartate aminotransferase
BNPC Bis(4-nitrophenyl) carbonate
DCE 1,2-dichloroethane
DCM dichloromethane
DIEA N,N-diisopropylethylamine
DMI 1,3-dimethyl-2-imidazolidinone
EDCI 1-ethyl-3-[3-(dimethylamino)propyl]carbodiimide hydrochloride
EP Endo Porter, a peptide delivery composition (Gene Tools, LLC)
EtOAc ethyl acetate
HMDS hexamethyldisilazane
HOBT 1-hydroxybenzotriazole hydrate
L linking group
MeCN acetonitrile
MeOH methanol
MW molecular weight
PG protecting group
RT room temperature
TBME t-butyl methyl ether
TEA triethylamine
TFA trifluoroacetic acid
TFE 2,2,2-trifluoroethanol
THF tetrahydrofuran
TLC thin layer chromatography
Tr trityl
VM Vivo-Morpholino commonly referred to a conjugate of transporter composition of this invention and a morpholino oligo.

II. General

The present invention relates to the finding that guanidine residues provide an enhanced transport of drugs and other agents across biological membranes when the residues are part of an oligoguanidine that provides suitable assembly of the guanidines. This is in contrast to the previously described polymers of, for example, arginine, in which the guanidine moieties are present on essentially all subunits of the linear transport polymer. This is also different from the previously described dendrimers of guanidines, in that the guanidine moieties in the present invention are assembled on a triazine scaffold. Thus, the transporter oligomers of the present invention can be viewed in one group of embodiments as polymers in which guanidine residues are present, but spaced by dendrimeric branches such that each guanidine moiety is in the terminal head group of side chains. Synthetically, the side chains can be selected to enhance the freedom of the arm length and adjust the lipophilicity of the transporter oligomer. Furthermore, the central amino group can provide a site for attachment to a linking group which can conjugate with bioactive substances. More importantly, guanidine moieties are prepared from their amine precursors, which are transformed by a single step perguanidinylation. This process takes the advantage of avoiding using the expensive reagent as compared with the prior art which involves use of costly reagents for conversion and protection of guanidines. The whole assembly of the transporter composition and its joining to the bioactive compound was designed in a concise manner which can be implemented simply and cost-effectively.

III. Transporter Composition

Bioactive Substance Conjugate

As noted above, the present invention provides compositions and methods that enhance the transport of bioactive substances across biological membranes. The compositions are represented by the structures containing triazine as scaffold, oligoguanidine as head groups of each side chains and bioactive substances attached to a linking group. Accordingly, the invention also includes the oligoguanidine compounds described herein that are chemically tethered to a bioactive substance (which includes therapeutic agents and prodrugs thereof).

The oligoguanidine compounds can be tethered to the therapeutic agent in a variety of different ways. The therapeutic agents can be linked to a transporter composition of the invention in numerous ways, including a direct bond or by means of a linking moiety. In particular, carbamate, amide, ester, thioether, disulfide, and hydrazone linkages are generally easy to form and suitable for most applications. In addition, various functional groups (e.g., hydroxyl, amino, halogen, etc.) can be used to attach the therapeutic agent to the transporter composition. For those therapeutic agents that are inactive until the attached transporter composition is released, the linker is preferably a readily cleavable linker, meaning that it is susceptible to enzymatic or solvent-mediated cleavage in vivo. For this purpose, linkers containing carboxylic acid esters and disulfide bonds are preferred, where the former groups are hydrolyzed enzymatically or chemically, and the latter are severed by disulfide exchange, e.g., in the presence of glutathione.

Therapeutic agents that benefit from the transporter composition of the invention include both small organic molecules and macromolecules (e.g., nucleic acids, oligonucleotides and the analogs thereof, Morpholinos and peptide nucleic acids, polynucleotides, peptides, polypeptides, and proteins). Exemplary therapeutic agents include local and systemic anti-cancer agents, antibiotics, antisense drugs, protease inhibitors, and so forth. In addition, there are numerous releasable linkers that can be used with the transporter composition of the invention, which can be cleaved by phosphatases, proteases, esterases, redox compounds, photochemical agents, nucleophilic agents, acidic compounds, and so forth. Release of the therapeutic agent can be the result of either enzymatic or non-enzymatic action.

Turning next to the bioactive substance, the present invention finds broad application to essentially any therapeutic or diagnostic agent. Examples of therapeutic compounds include, without limitation, the following: oligonucleotides and polynucleotides formed of DNA and RNA; oligonucleotide analogs such as phosphonates (e.g., methyl phosphonates), phosphoramidates, thiophosphates, locked nucleic acids (LNA), uncharged Morpholinos and peptide nucleic acids (PNAs) or their structural variations containing positive or negative charges; proteins such as kinase C, RAF-1, p21Ras, NF-κB and C-JUN; and, polysaccharides and polysaccharide analogs. Diagnostic agents include both diagnostic imaging agents and contrast agents. The following are non-limiting examples of diagnostic agents: radio-labeled substances such as $^{99}$mTc glucoheptonate; substances used in magnetic resonance imaging such as gadolinium doped chelation agents (e.g., Gd-DTPA); metals bound to chelating agents such as Eu, Lu, Pr, Gd, Tc$^{99}$m, Ga$^{67}$, In$^{111}$, Y$^{90}$, Cu$^{67}$ and Co$^{57}$; and proteins such as β-galactosidase, green fluorescent protein and luciferase. Still other useful agents include dyes such as, for example, fluorescein.

In certain embodiments, the transporter composition is attached to the bioactive substance through a linking moiety. Such a linking moiety has two termini, one that covalently bonds to the transporter composition and one that covalently bonds to the bioactive substance. The termini each contain a functional group that serves as a facile point of attachment. Examples of such groups include, without limitation, carboxylic acid, carboxylic acid derivatives, alcohols, amines and thiols. For example, suberic acid is a linking moiety having a carboxylic acid at each terminus. One terminus is used in attaching the transporter composition, while the other in attaching the bioactive substance.

The linking moiety is preferably cleaved in vivo. "Cleaved" in this case refers to separation of a linking moiety from the bioactive substance. The separation is effected through cleavage of a covalent bond. For instance, a linking moiety containing a disulfide bond may be cleaved in the reducing environment in the cells of a living organism, resulting in the separation of transporter composition from the bioactive substance. Or a linking moiety contains a short section of peptide, which can be cleaved by proteases in the living organism. The cleavage releases a free bioactive substance from the transporter composition.

IV. Synthesis of Transporter Moieties and Compositions

A. General Reaction

FIG. 1 provides an illustration for the synthesis of a dendrimeric octaguanidine beginning with monoprotected piperazine 1. The protected piperazine 1 reacts with cyanuric chloride to give monosubstituted dichlorotriazine. The dichloride is then treated with diethanolamine to give tetraalcohol 4. The hydroxyl groups are activated with a suitable activating reagent to provide tetracarbonate 5. The tetracarbonate 5 is treated with a secondary amine 2 obtained from selective protection for primary amines of a triamine to tetracarbamate 6 containing octaamine in a protected form. The secondary amine of piperazine 7 is regenerated by deprotection, which reacts with an activated linker 3 to give the transporter moiety 8 with an active functional moiety at one terminus. This active functional group 8 couples with a bioactive substance to give a conjugate 9. The final removal of protecting groups to give octaamine 10 and perguanidinylation thereof fulfills the whole entity assembly for a transporter-enabled bioactive substance 11. More detail below is provided for perguanidinylation.

Figure 2:
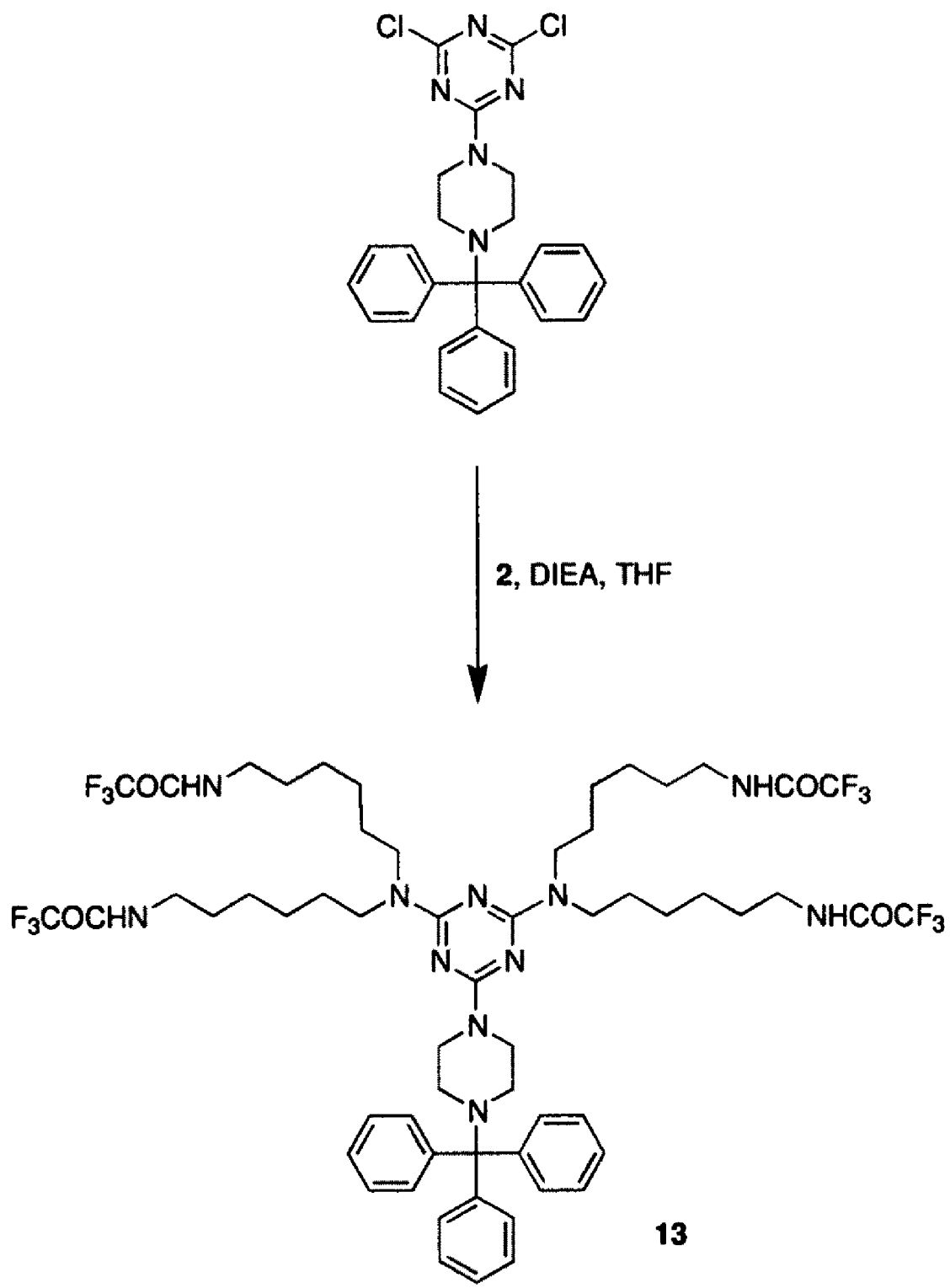
FIG. 2 illustrates a synthetic scheme of assembling a protected central nitrogen functional group and a triazine scaffold containing four side chains each with a protected primary amine.

FIG. 2 illustrates a synthetic scheme of assembling a protected central nitrogen functional group and a triazine scaffold containing four side chains each with a protected primary amine. The monosubstituted dichlorotriazine is treated with a secondary amine 2 obtained from selective protection for primary amines of a triamine to give an entity containing triazine as scaffold and four primary amines in a protected form 13.

Figure 3:
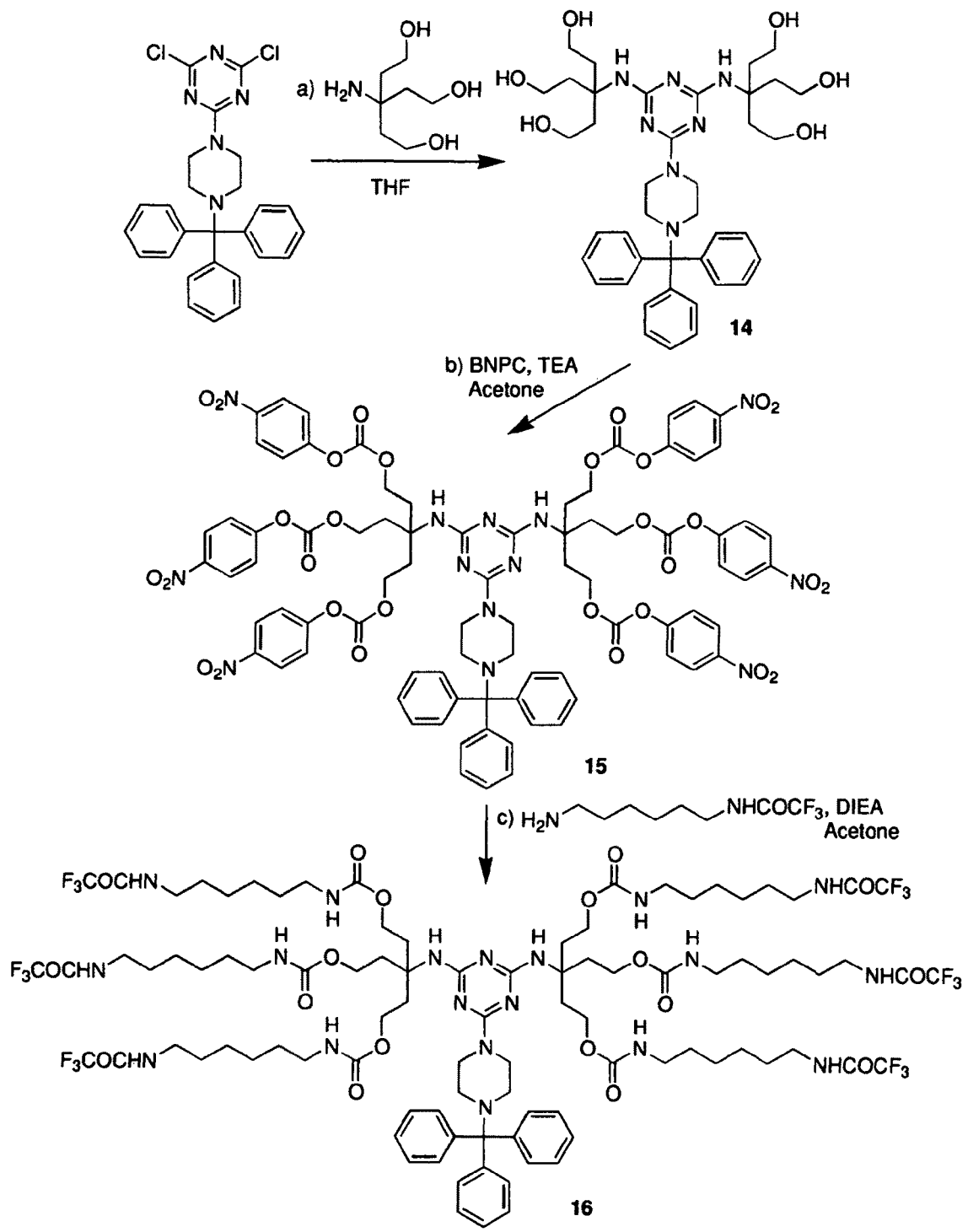
FIG. 3 illustrates a synthetic scheme of assembling a protected central nitrogen functional group and a triazine scaffold containing six side chains each with a protected primary amine. The multiplication of the side chains takes the advantage of aminotriol, where the amino group reacts with the dichloro triazine derivative and the resultant hexa-alcohols are activated to form reactive carbonate. The carbonates are then treated with suitably protected amines to give hexa-primary amines in a protected form.

FIG. 3 illustrates a synthetic scheme of assembling a protected central nitrogen functional group and a triazine scaffold containing six side chains each with a protected primary amine. The monosubstituted dichlorotriazine is treated with aminotrialcohol to give hexa-alcohol intermediate 14 which is activated to form the corresponding carbonate 15. The carbonate 15 is then treated with suitably protected amines to give hexa-primary amines in a protected form 16.

Figure 4:
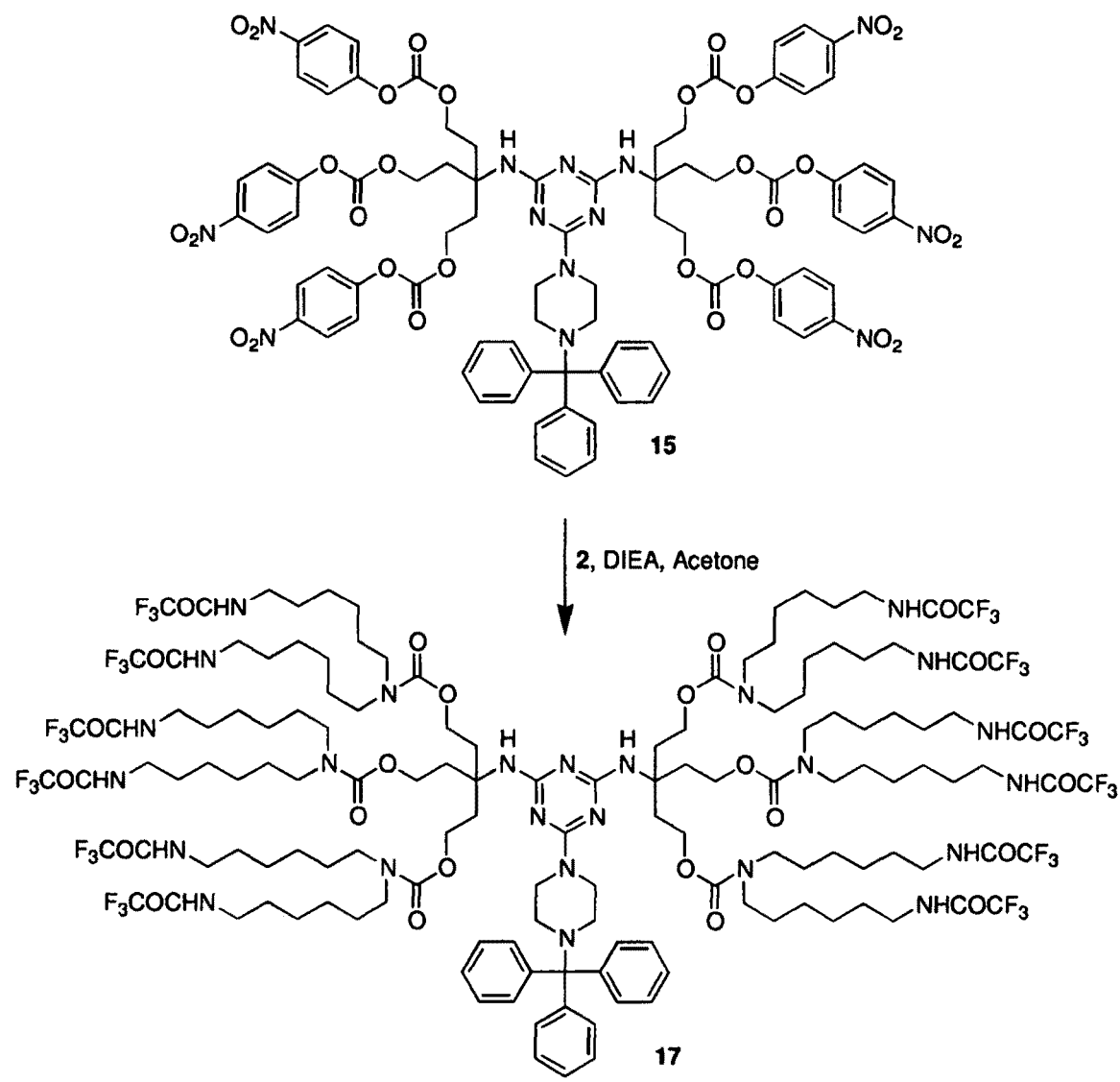
FIG. 4 illustrates a synthetic scheme of assembling a protected central nitrogen functional group and a triazine scaffold containing twelve side chains with a protected primary amine. By using the same reactive carbonate intermediate as shown in FIG. 3, and introducing a triamine containing a reactive secondary amine and two suitably protected primary amino groups, a dozen of side chains each with a protected primary amine are furnished.

FIG. 4 illustrates a synthetic scheme of assembling a protected central nitrogen functional group and a triazine scaffold containing twelve side chains with a protected primary amine. By using the same reactive carbonate intermediate 15 as shown in FIG. 3, and introducing a secondary amine 2 obtained from selective protection for primary amines of a triamine, a dozen of side chains each with a protected primary amine are furnished to afford compound 17.

Figure 1B:
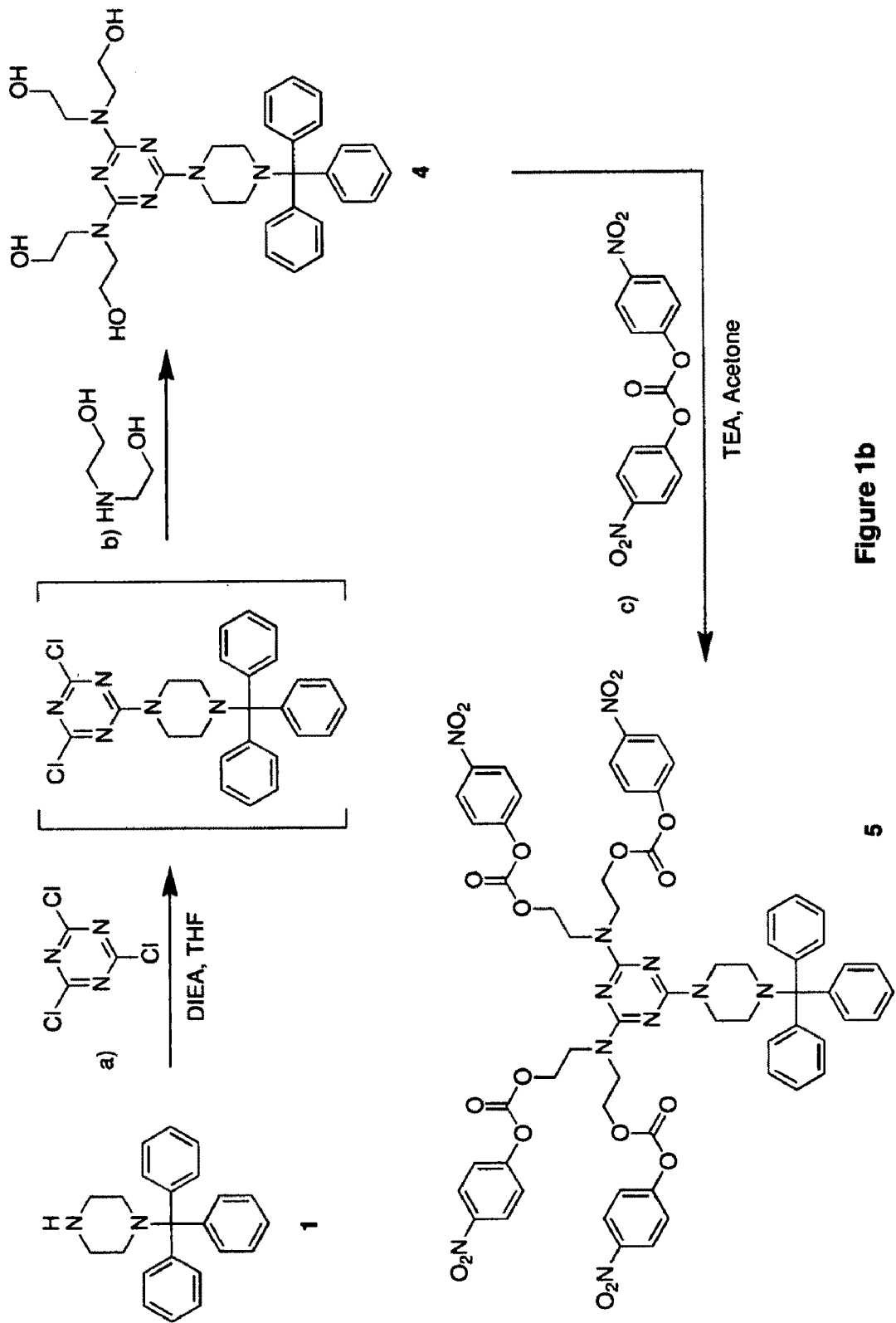
Figure 1C:
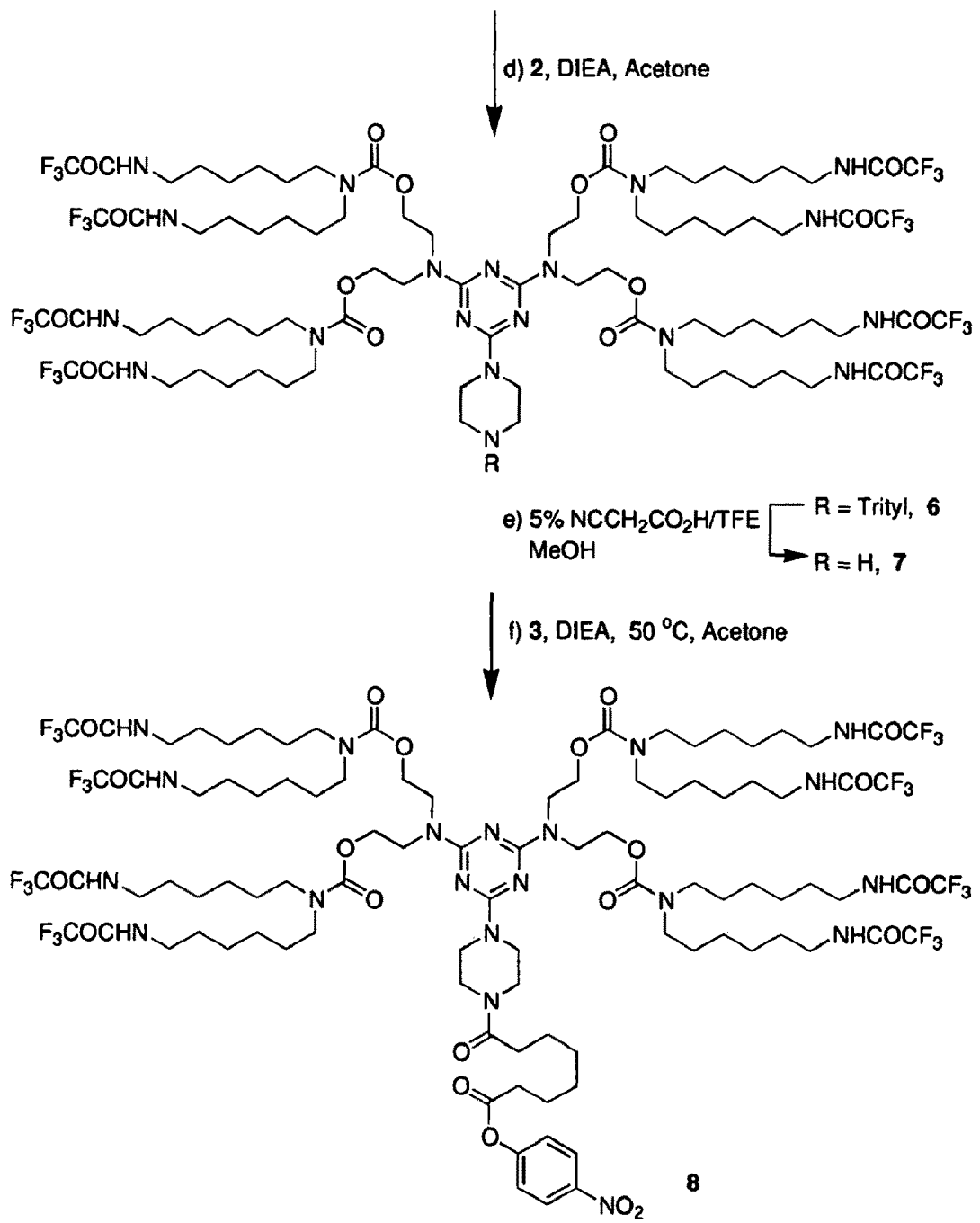
Figure 1D:
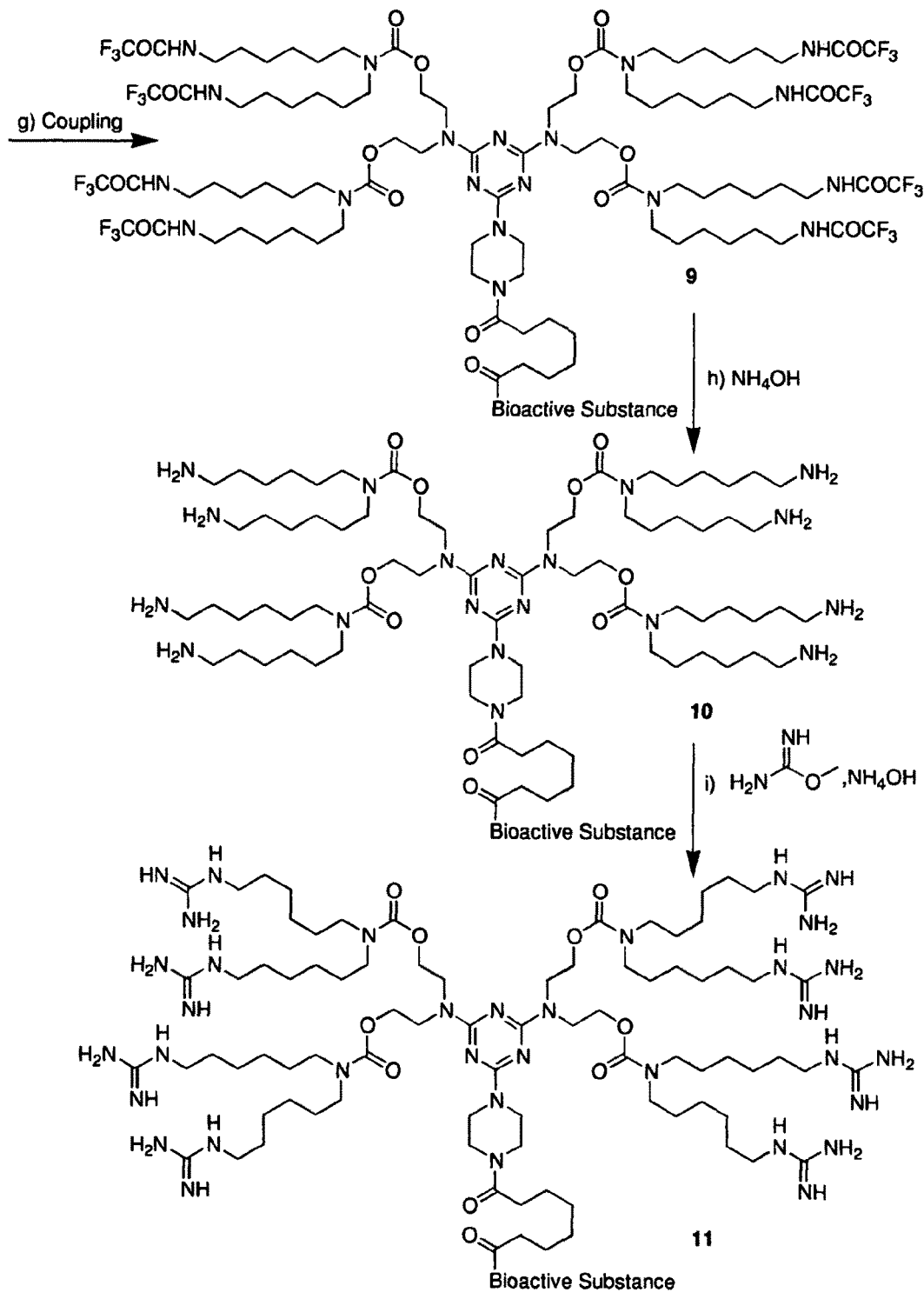
Figure 1E:
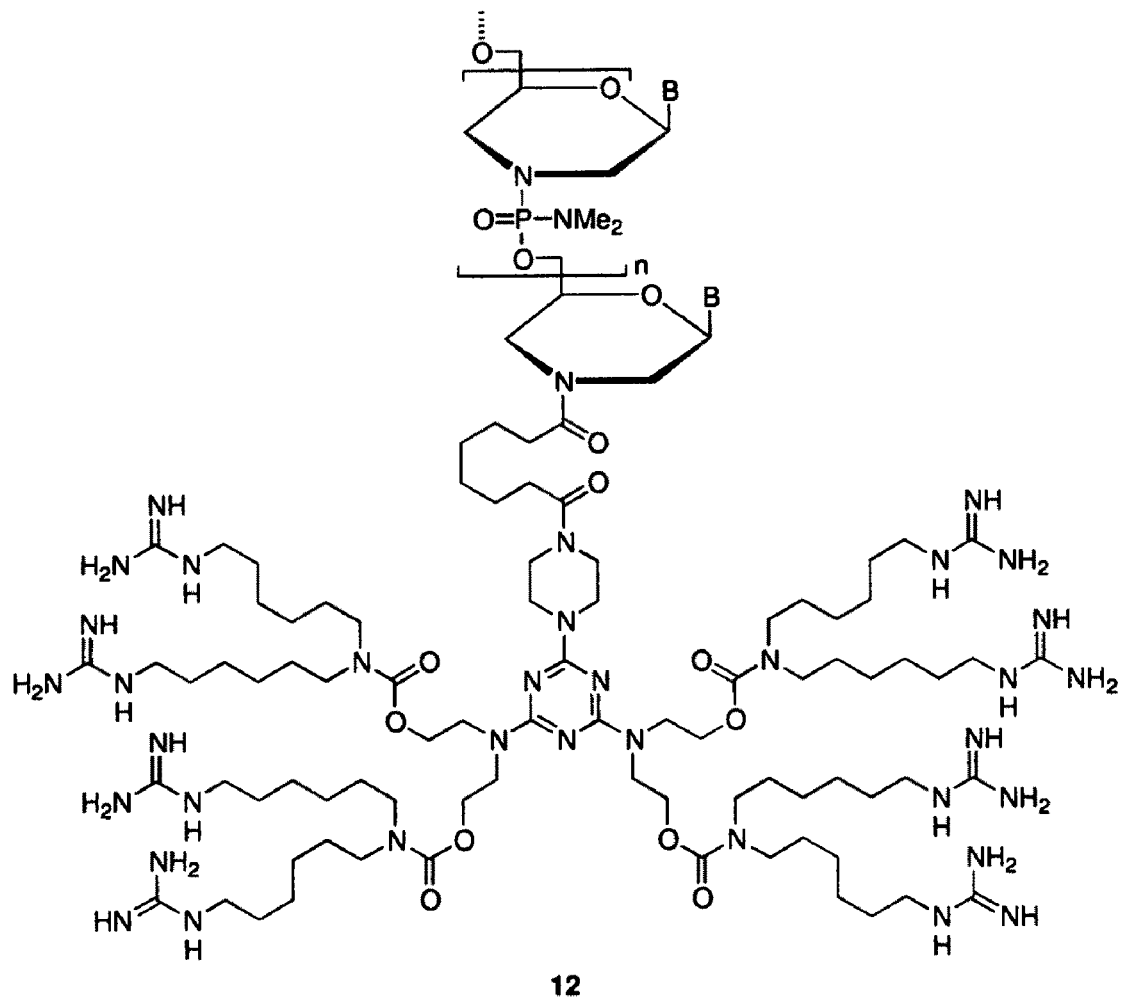
Figure 5:
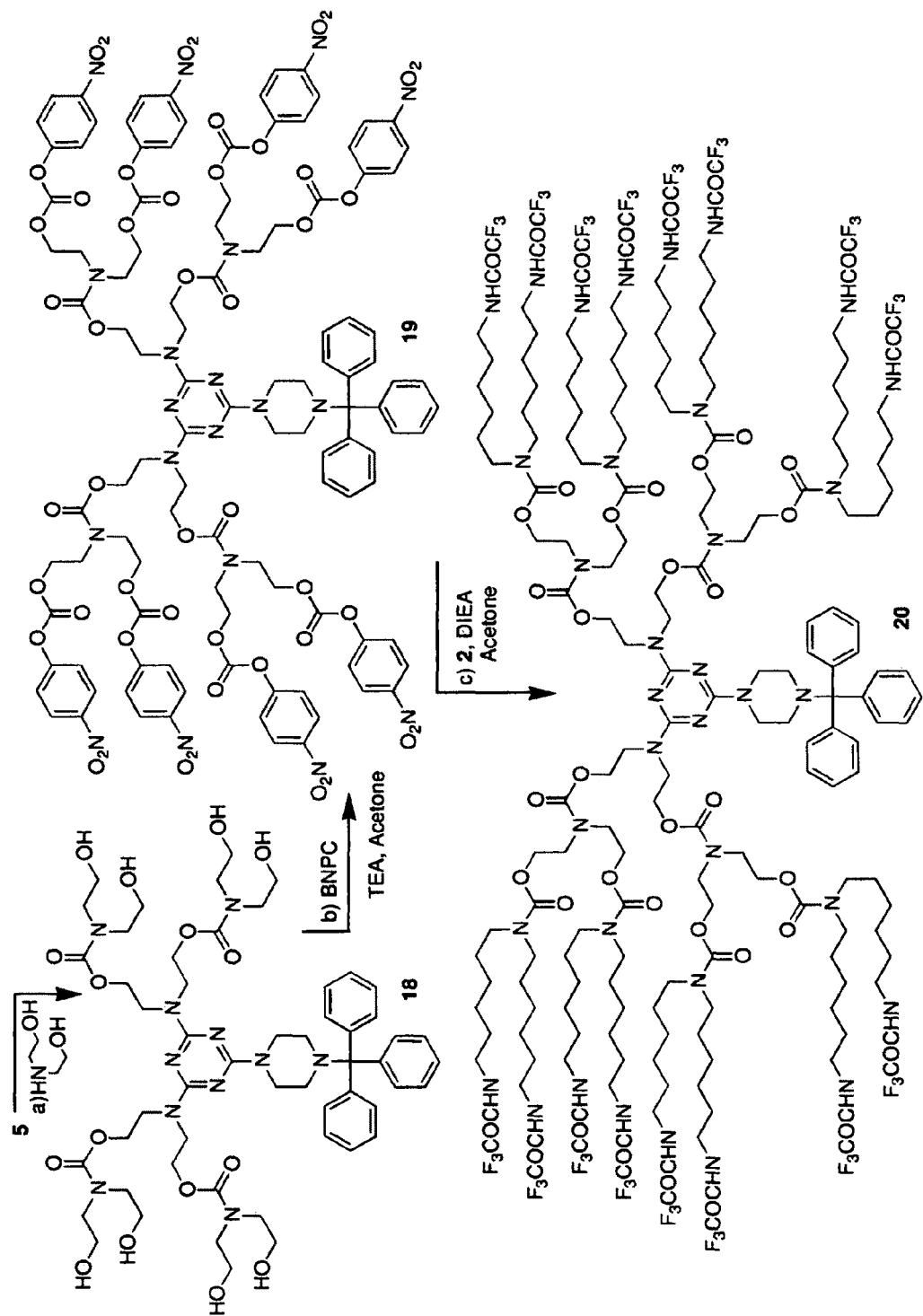
FIG. 5 illustrates a synthetic scheme of assembling a protected central nitrogen functional group and a triazine scaffold containing sixteen side chains with a protected primary amine. By using the same reactive carbonate intermediate as shown in FIG. 1b, treatment of diethanolamine gives octa-alcohol. Activation of the alcohol to the corresponding carbonate intermediate, followed by introduction of a triamine containing a reactive secondary amine and two suitably protected primary amino groups gives a triazine scaffold containing sixteen side chains each with a protected primary amine.

FIG. 5 illustrates a synthetic scheme of assembling a protected central nitrogen functional group and a triazine scaffold containing sixteen side chains with a protected primary amine. By using the same reactive carbonate intermediate 5 as shown in FIG. 1b, treatment of diethanolamine gives octa-alcohol 18. Activation of the alcohol 18 to the corresponding carbonate intermediate 19, followed by introduction of a secondary amine 2 obtained from selective protection for primary amines of a triamine, gives a triazine scaffold 20 containing sixteen side chains each with a protected primary amine.

Figure 6:
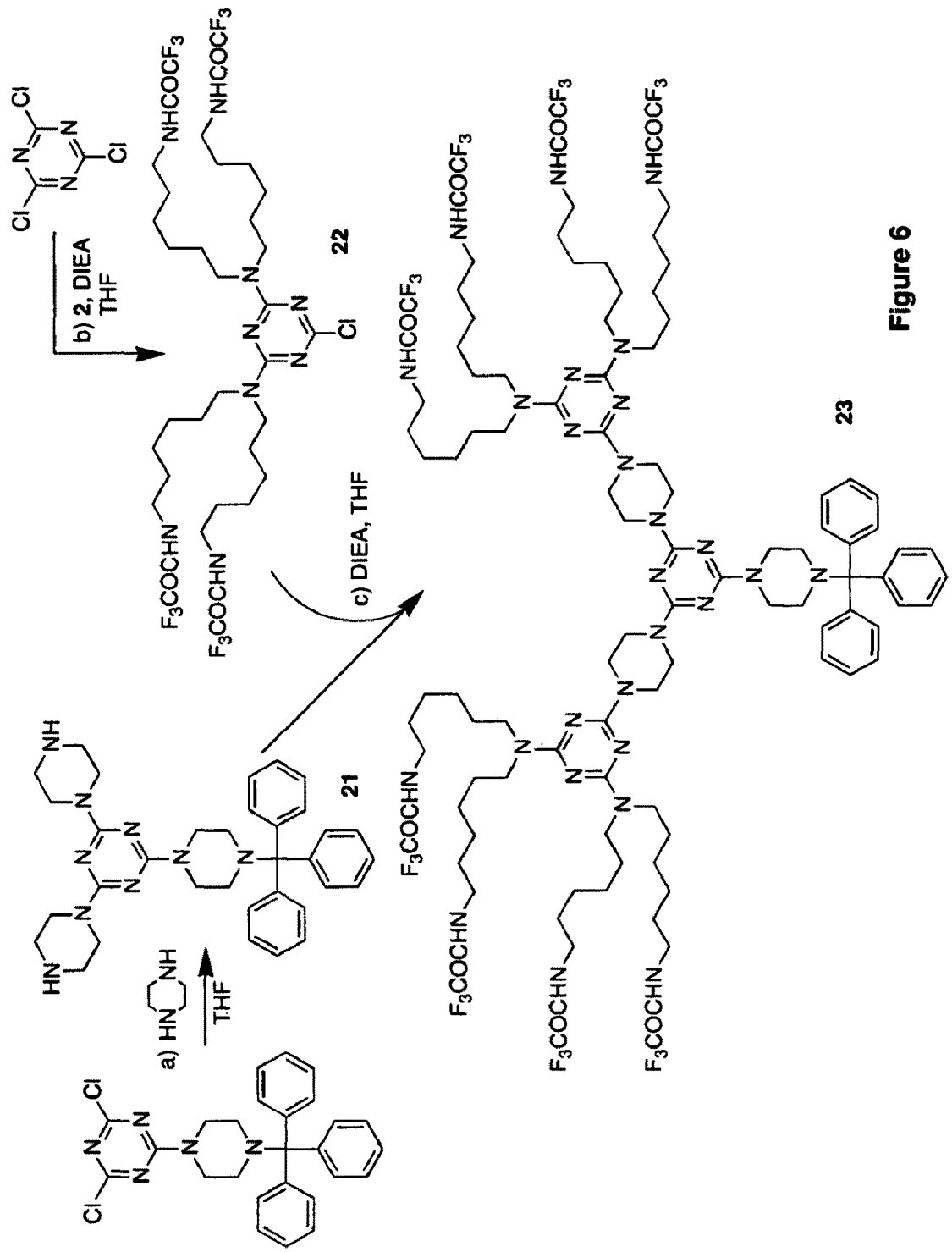
FIG. 6 illustrates a synthetic scheme of assembling a rigid core scaffold containing eight side chains each with a protected primary amine and a protected central nitrogen functional group. This scheme takes advantage of the relative reactivities of cyanuric chloride in such a way that mono-substituted dichlorotriazine can be converted to a diamine derivative as nucleophile to attack a di-substituted monochlorotriazine to form a dendrimeric structure containing eight side chains in a rigid core.

FIG. 6 illustrates a sequence for construction of a rigid core scaffold of octaamines in a protected form. The monosubstituted dichlorotriazine is treated with piperazine to give di-secondary amine 21. Disubstituted monochlotriazine 22, obtained from treatment of cyanuric chloride with the secondary amine 2 by a controllable manner, reacts with the di-secondary amine 21, resulting in a fully protected form of octaamine 23.

Figure 7:
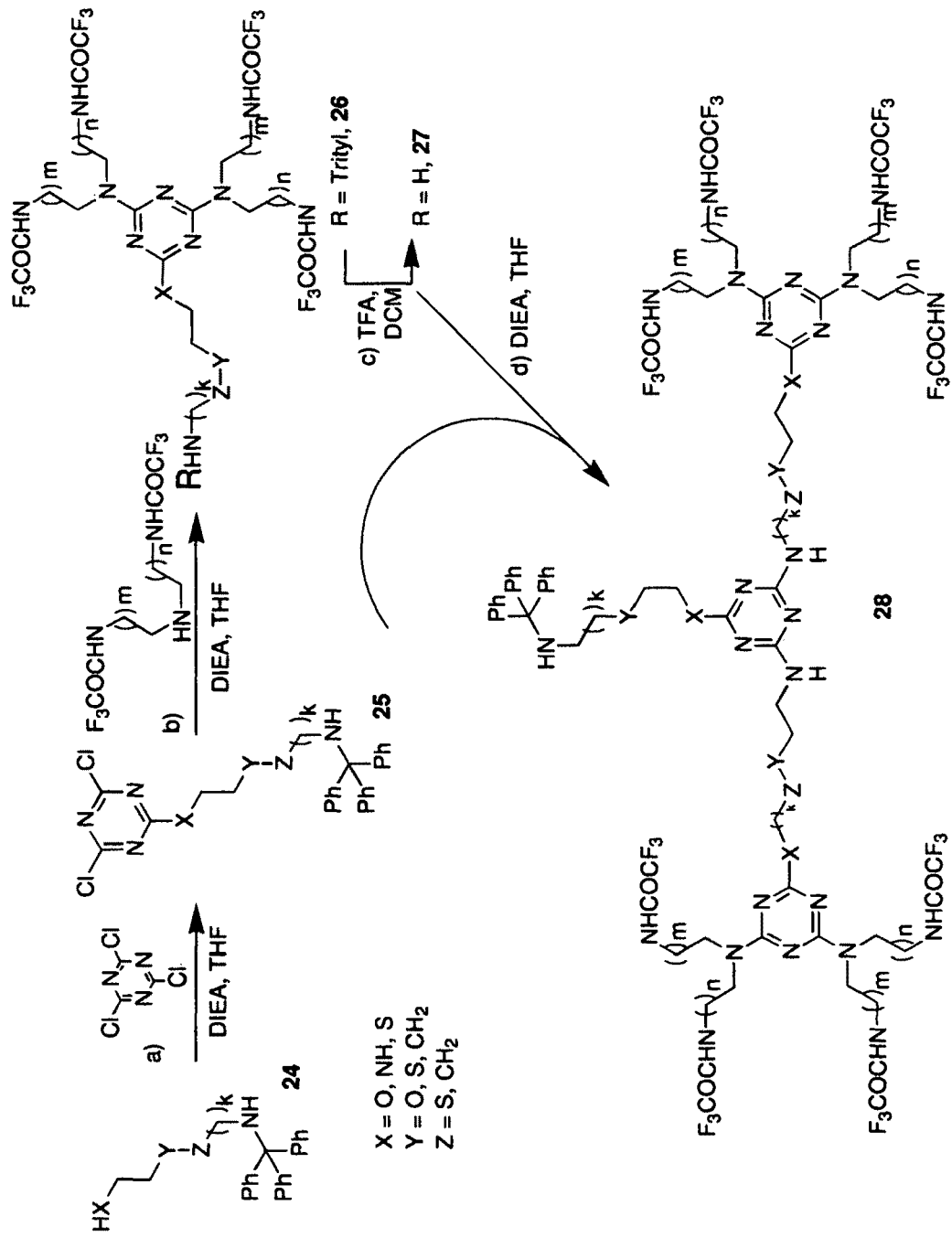
FIG. 7 illustrates a synthetic scheme of assembling a flexible core scaffold containing eight side chains each with a protected primary amine and a protected central nitrogen functional group. This scheme takes advantage of trisubstituted triazine containing a leash which the terminal amine, after deprotection, can be used as nucleophile to attack its own precursor, monosubstituted dichlorotriazine, to form a scaffold containing eight side chains each with a protected primary amine.

FIG. 7 illustrates a sequence for construction of a flexible scaffold of octaamines in a protected form. Reaction of monoprotected alcohol or amine 24 with cyanuric chloride gives monosubstituted dichlorotriazine 25, which is further exposed with two equivalents of secondary amine to give trisubstituted triazine 26. Removal of the trityl group generates a primary amine 27, which is again treated with the monosubstituted dichlorotriazine 25 to yield a fully protected form of octaamine 28.

Figure 8:
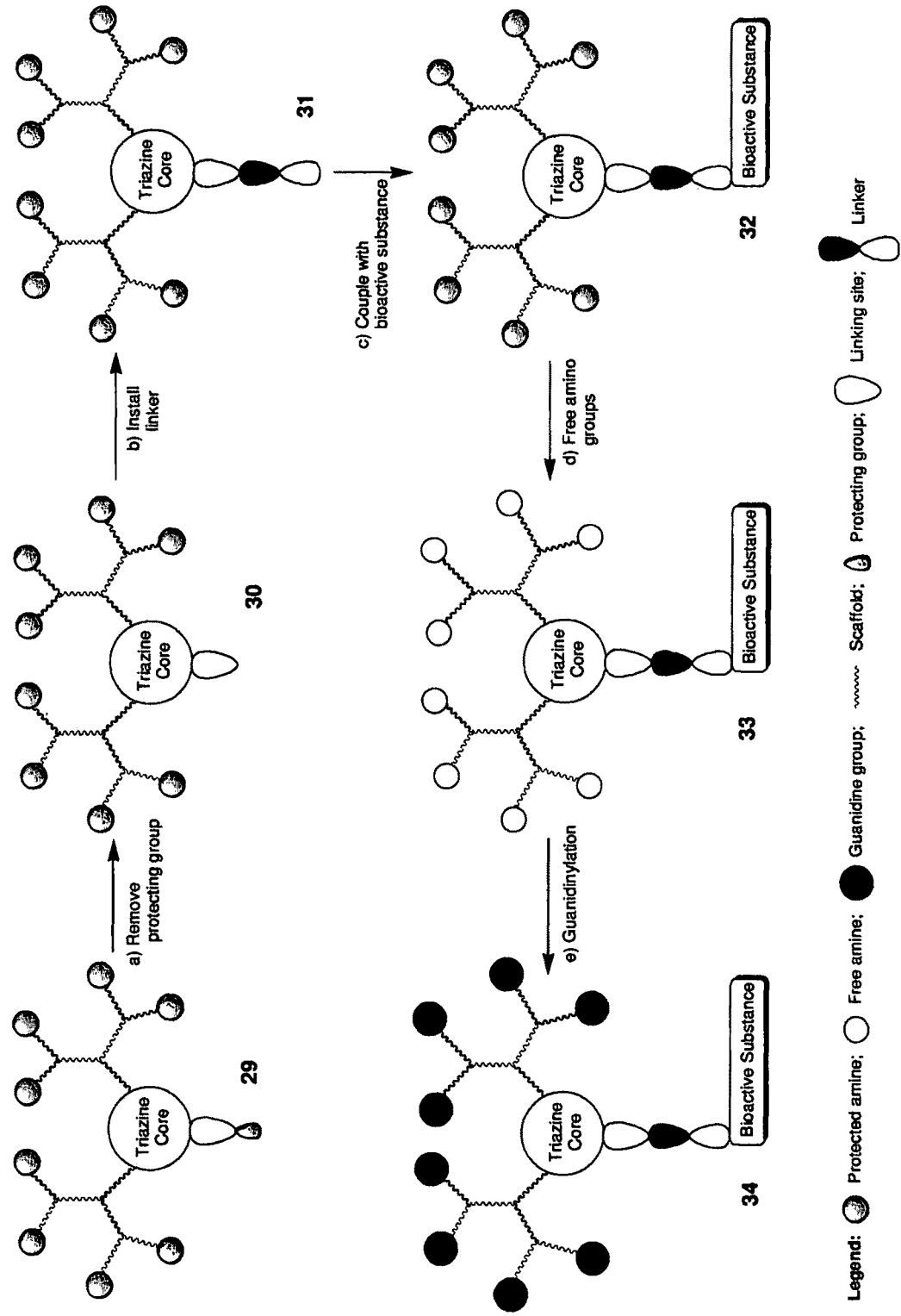
FIG. 8 illustrates a general scheme following FIGS. 2, 3, 4, 5, 6 and 7 for subsequent manipulation. The linking site generated after deprotection, is coupled with a linking group. The active end of the linking group is connected with a bioactive substance. The oligoamines, generated from removing the protecting groups, undergoes guanidinylation to give an oligoguanidine conjugated with bioactive substance.

As can be seen from FIGS. 1 to 7, use of triazine as a scaffold can assemble oligoamines in an efficient manner. All these amino groups are orthogonally protected (trityl vs. trifluoroacetyl). Removal of trityl group provides a site for installing a linking group which can be used for conjugation with bioactive substance. FIG. 8 illustrates a general scheme following FIGS. 2, 3, 4, 5, 6 and 7 for subsequent manipulation. The linking site of 30, generated after deprotection of 29, is coupled with a linking group to afford 31. The active end of the linking group of 31 is connected with a bioactive substance to give a conjugate 32. The oligoamine 33, generated from removing the protecting groups of 32, undergoes guanidinylation to give 34, an oligoguanidine conjugated with bioactive substance.

Figure 9:
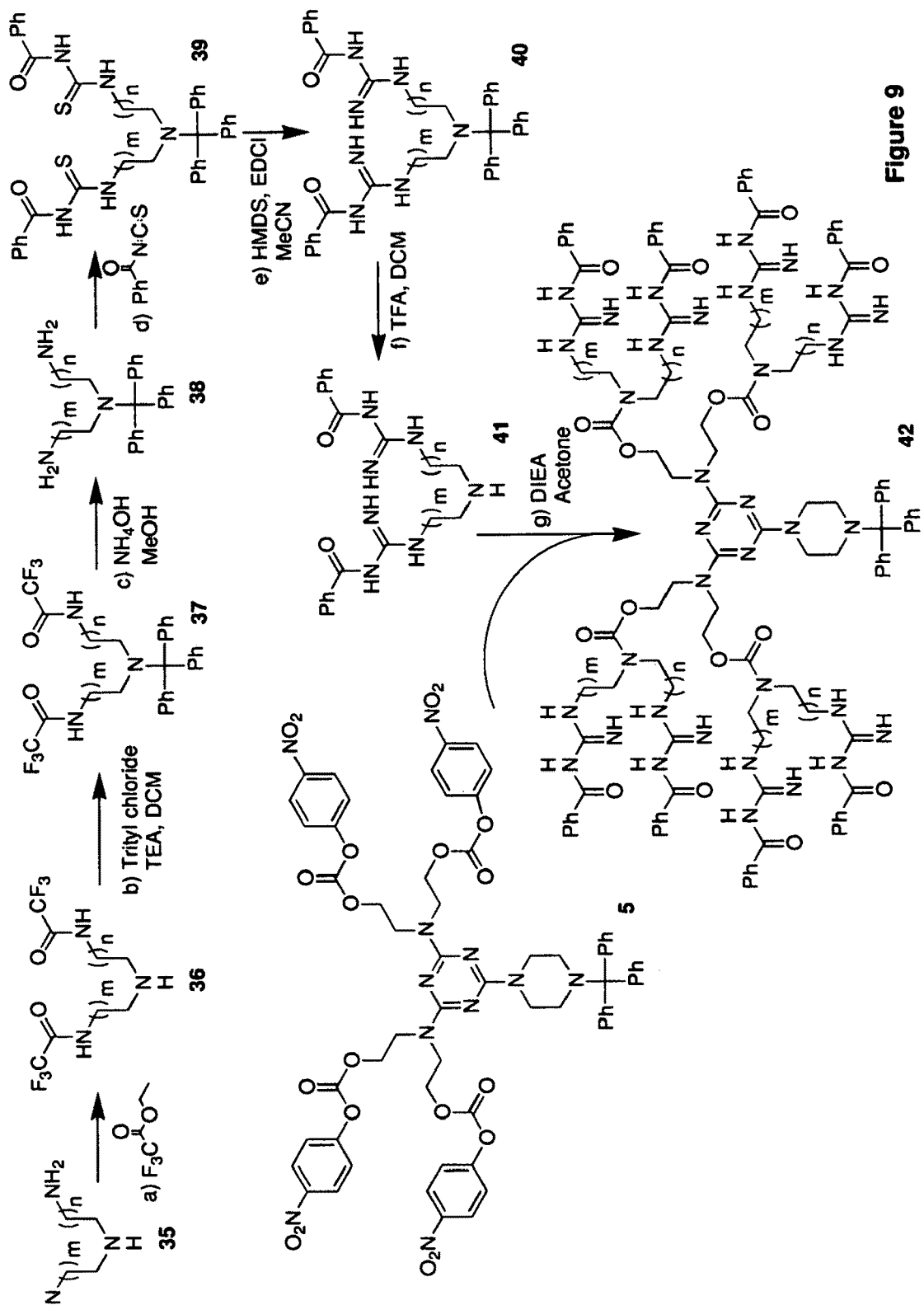
FIG. 9 illustrates one scheme of assembling oligoguanidine in a pre-formed manner. Therefore, this strategy represents the complementary method of installing guanidine prior to conjugation with a bioactive substance. The same deprotection strategy is applied for generating the central reactive nitrogen for installation of a linker and subsequent conjugation with a bioactive substance.

FIGS. 1 to 7 also show the same methodology which requires a deprotection and perguanidinylation process after conjugation with bioactive substance. FIG. 9 illustrates a sequence where guanidine groups are built-in before the transporter composition is coupled with bioactive substance. This is very useful for those bioactive substances which are vulnerable to the conditions used for perguanidinylation. The selective protection of primary amine 35 with trifluoroacetyl group gives free secondary amine 36 which is orthogonally protected with trityl group to give intermediate 37. The primary amine 38 re-generated by deprotection can be transformed to guanidine 40 in a protected form. Removal of the trityl group gives the secondary amine 41 which reacts with the carbonate intermediate 5 to furnish the octaguanidine 42 in a protected form.

Although the transformation described in FIG. 9 is useful for some bioactive substances which are vulnerable to the conditions used for perguanidinylation, one of skill in the art will readily understand that this route is rather lengthy whereas post-coupling perguanidinylation is the cost-effective way. As a matter of fact, in one embodiment of the invention, the deprotection and perguanidinylation is carried out in a single reaction vessel without intermediate purification, providing a practical process for efficient streamlined production of conjugate containing transporter composition and bioactive substance.

B. Specific Embodiments of the Methods of the Invention

Accordingly, one embodiment of the invention is a method for the preparation of an oligoguanidine compound, comprising contacting an oligomer having chemically tethered amines, at least a portion of which are protected, with a protecting group removal agent and a guanidinylation reagent to convert each of said protected amines to a guanidinyl group, to produce an oligoguanidine compound. More specifically, the method may comprise the steps of (a) assembling a dendrimeric structure using triazine as a core scaffold to install a plurality of side chains each containing a chemically tethered amine, (b) contacting one amino group which is orthogonally protected to the amino groups at the end of each side chain with a linking group having reactive functional entities on each end. The linking group having the remaining reactive functional entity is conjugated with a bioactive substance, (c) contacting an oligomer having a plurality of chemically tethered amines, wherein a portion of the tethered amines have attached protecting groups, with a protecting group removal agent to remove the protecting groups to produce an oligomer having a plurality of chemically tethered amines; and (d) contacting the resulting oligomer with a guanidinylation reagent to convert each of the chemically tethered amines to a guanidinyl group to produce an oligoguanidine compound.

In some embodiments, the oligomer having chemically tethered amines will be isolated and purified using methods such as ion exchange chromatography, HPLC, column chromatography and the like. This oligomer (tethered amine) compound can be isolated as a salt or in neutral form. However, in a preferred embodiment, the oligomer compound having chemically tethered amines is not isolated, but is carried on directly to step (d) In certain embodiments, steps (c) and (d) are carried out in the same reaction vessel. Therefore, an oligomer compound having protecting groups on each of the amines can be treated with a protecting group removal agent and subsequently a guanidinylation reagent to provide the oligoguanidine compound in a single vessel. In one particularly preferred embodiment, an oligomer having trifluoroacetyl protecting groups on each of the ω-amines is contacted with a protecting group removal agent, preferably aqueous ammonia solution, and afterwards with a guanidinylation reagent, preferably O-methylisourea hydrochloride.

In other embodiments, the oligomer having chemically tethered amines is a dendrimeric scaffold with a triazine as the center piece. In another embodiment, the branching moiety from triazine is dialcoholamine (wherein "dialcoholamine" refers to those compounds having hydroxyl group at each end of the side chains and the side chains containing multiple methylene and other heteroatom such as O, S, B and the like.)

In one particularly preferred embodiment, diethanolamine is used for multiplication of the side chains. The nitrogen atom from the dialcoholamine connects to the triazine core and the hydroxyl groups from the alcohols develop further for a plurality of side chains. The multiplication of side chains is preferably enabled by formation of carbonate intermediate, which is in turn preferably connected with a secondary amine of bis(hexamethylene)triamine wherein both primary amines are protected with preferably trifluoroacetyl groups.

Another embodiment of the invention is a method for the preparation of an oligoguanidine compound from a suitably protected oligoamine, comprising the steps of: (a) connecting two dialcoholamine to monosubstituted dichlorotriazine to produce a tetraalcohol; (b) activating each of the hydroxyl group of the tetraalcohol to form carbonate intermediate; (c) treating each of the carbonate groups with dialcoholamine to generate an octahydroxyl compound and thereafter activating each of the hydroxyl group of the octahydroxyl to octacarbonate; (d) subjecting the carbonate compound with a secondary amine of bis(hexamethylene)triamine wherein both primary amines are protected with preferably trifluoroacetyl groups to give oligoamines in a protected form. When step (c) is done once, an oligomer is obtained which has sixteen side chains each containing a primary amine in a protected form. In one particularly preferred embodiment, step (c) is skipped and step (d) is conducted directly after step (b) to give an oligomer having eight side chains each containing a primary amine in a protected form.

C. Exemplary Method of the Invention

Perguanidinylation has been described for the preparation of cationic oligonucleotides (Deglane, G. et al. *Chem Bio Chem* 7:684-692 (2006)). Perguanidinylation has now been found to have utility in the preparation of oligoguanidine transporter composition as described herein.

For example, a suitable synthesis of the guanidine octamer was desired due to the utility of this compound as a membrane transport reagent. In view of the perguanidinylation studies noted above, octaguanidine could in principle be prepared from an octaamine through a late stage perguanidinylation reaction. The primary amino groups can be transformed to guanidines by final perguanidination, a step offering additional advantages of avoiding the use of expensive protecting groups for the guanidinium subunit if it is pre-formed otherwise.

Selective protection of a triamine having a secondary amine in the middle or close to the middle of the chain and two primary amines on each end of the chains can be achieved to give the free secondary amine and the protected primary amines. This strategy can make use of a triamine for connecting the secondary amine to a core scaffold and for converting two primary amines to a couple of guanidines at the final stage. In order to manipulate the chemistry in an orthogonally protected manner, base-labile trifluoroacetamide protecting group is incorporated on the primary amine for the ultimate conversion to guanidine after deprotection, and acid-labile trityl protecting group is installed on the amine for the linkage with a leash connecting with a bioactive substance. The requisite mono-tritylated piperazine used for starting the construction of a triazine core scaffold is prepared by exposing trityl chloride with excess amount of piperazine. After treatment of tritylpiperazine with cyanuric chloride, diethanolamine is used to doubling the functional site. The tetrralcohol thus formed is activated to give tetracarbonate by using bis (4-nitrophenyl) carbonate. Reaction of the tetracarbonate with the secondary amine of a triamine having the primary amines protected with trifluoroacetyl group gives rise to the octaamine in a protected form. Removal of the trityl group is achieved by acid treatment. The free amine thus generated is exposed to a large excess of linking reagent, suberic di(4-nitrophenyl) ester, resulting in the connection of the octaamine with the linking moiety and yielding an active ester for subsequent conjugation with a bioactive substance.

After conjugation of the octaamine with a bioactive substance through a linking moiety, the final deprotection and perguanidinylation can be accomplished via a single vessel operation. Since ammonia has been utilized to effect the deprotection of trifluoroacetamides, and also as one of the reagents in the guanidinylation of amines, a single vessel operation was investigated. Thus, treatment of the octaamine derivative with concentrated ammonia gives a conjugate of octaamine and the bioactive substance. Without purification, the mixture is treated further with O-methylisourea hydrochloride with additional 18% ammonia solution to give octaguanidine coupled with a bioactive substance. The conversion of octaamine to octaguanidine by using this guanidinylation system is virtually quantitative and the purification can be carried out by using Oasis HLB LP extraction cartridge (Waters Corporation, Milford, Mass., US).

Significantly, eight trifluoroacetamides were removed to eight primary amines and subsequently converted to eight guanidines under mild conditions in quantitative yield. And more significantly, the ammonolytic deprotection, and subsequent perguanidinylation carried out in a single reaction vessel, without intermediate purification, enables the practical streamline production of conjugate containing bioactive substance and transporter composition. This process improvement constitutes a very valuable and cost-effective advantage over prior art production procedures.

D. Protecting Groups and Protecting Removal Agents

The precise conditions and reagents or agents used in the process will depend on the nature of the protecting groups to be kept or removed. Protecting groups selected for the protection of the chemically tethered amine groups on the side chains are generally those groups that can be distinguished from the other protecting groups in other portions of the molecule (e.g., the trityl group protecting the amino group for linking the leash with a bioactive substance). Such protecting groups are often referred to as "orthogonal". Generally, the reagents and conditions can be employed by following the guidelines in such protecting group treatises as Wuts and Greene, Protective Groups in Organic Synthesis, 4 th ed., John Wiley & Sons, New York N.Y. (2007), and the references cited therein.

As noted above, the method of the invention involves contacting an oligomer having a plurality of chemically tethered amines, with a protecting group removal agent to remove the protecting groups.

In one embodiment of the invention, trifluoroacetyl group is selected for the protecting groups on each of the chemically tethered amines for four critical reasons: (a) methyl or ethyl trifluoroacetate is a mild and selective reagent to protect primary amines in the presence of secondary amine, therefore, it is useful to keep the secondary amine intact while protecting the primary amine in a polyamine (a triamine in this particular case) so that the secondary amine can be used to connect to reactive functional groups in the scaffold; (b) a different amino group is used for linking the leash for conjugation with bioactive substance. Acid labile trityl group is selected for this amino group since trifluoroacetyl group is labile towards basic conditions but stable towards acidic conditions; (c) trifluoroacetyl protecting groups on the amines can be cleaved by ammonolysis, a condition also used for removing protecting groups in some bioactive substances. Therefore, exposure of ammonia can remove protecting groups both in the bioactive substance and in the oligoamine moieties. This strategy proves very useful in the cases where for example, coupling of the precursor transporter composition, i.e. oligoamine in a protected form, is carried out with Morpholino antisense oligo while it is still on the synthesis resin and subsequent ammonolytic treatment not only removes all the protecting groups on the Morpholino oligo and the oligoamine moiety, but also cleave the conjugate of precursor transporter composition and Morpholino from the synthesis resin. This advantage of convenience being able to cleave the conjugate from the synthesis resin and remove the protecting groups for subsequent guanidinylation paves the way for simple operation and economic production. (d) ammonia is also a reagent for converting amino group to guanidine in the presence of a guanidinylation agent, O-methylisourea hydrochloride. Therefore, without any purification, the ammonia used for deprotection of protecting groups in oligoamine can be carried over for the subsequent guanidinylation. By choosing the selected protecting groups and the selected protecting group removal agent, the whole production process for a conjugate containing a bioactive substance and transporter composition is significantly simplified and its cost is considerably reduced in comparison to prior art methods.

E. Guanidinylation Reagents

As noted above, the method of the invention involves contacting the oligomer having a plurality of chemically tethered amines, with a guanidinylation reagent to convert each of the chemically tethered amines to a guanidinyl group to produce an oligoguanidine compound.

Any guanidinylation reagent useful for converting an amino group to a guanidinyl group can be used in the present invention. Preferably, the guanidinylation reagent is a salt of O-methylisourea. Most preferably, the guanidinylation reagent is O-methylisourea hydrochloride. Other suitable guanidinylation reagents are described in Bernatowicz et al., J. Org. Chem. 57: 2497-2502 (1992).

EXAMPLES

The practice of the present invention will employ, unless otherwise indicated, conventional techniques of synthetic organic chemistry, biochemistry and the like, which are within the skill of the art. Such techniques are explained fully in the literature. See, for example, Kirk-Othmer's Encyclopedia of Chemical Technology; and House's Modern Synthetic Reactions.

The following examples are put forth so as to provide those of ordinary skill in the art with a complete disclosure and description of how to make and use the compositions/compound/methods of the invention. Efforts have been made to ensure accuracy with respect to numbers (e.g., amounts, temperature, etc.) but some experimental error and deviations should, of course, be allowed for. Unless indicated otherwise, parts are parts by weight, temperature is degrees centigrade and pressure is at or near atmospheric. All components were obtained commercially unless otherwise indicated.

Example 1

Synthesis of N-tritylpiperazine (1)

Piperazine (107.5 g, 1.25 mole) was dissolved in DCM (500 ml). Trityl chloride (69.7 g, 0.25 mole) was added to the mixture cooled in an ice bath. After addition, the mixture was kept at room temperature for 30 min. The mixture was washed with water (500 ml, three times). And the organic layer was separated and dried over sodium sulfate. The mixture was concentrated to ca. 100 ml and added to hexane (1 liter). The solid was removed by filtration. The filtrate was evaporated to dryness to give a white solid (ca. 100 g).

Example 2

Synthesis of bis(trifluoroacetamidohexyl)amine (2)

Bis(hexamethylene)triamine (8.62 g, 40 mmol) was dissolved in acetonitrile (120 ml). Water (0.864 ml) was added to the mixture. Ethyl trifluoroacetate (16.7 ml, 140 mmol) was added to the mixture cooled in an ice bath. After addition, the mixture was refluxed for 16 hours. The solvents were removed by evaporation. The residue solidified upon storing at room temperature and was used for next step without purification.

Example 3

Synthesis of di(4-nitrophenyl) suberate (3)

Suberic acid (8.71 g, 50 mmol) and 4-nitrophenol (14.61 g, 105 mmol) were dissolved in DCE (100 ml). 1,3-Diisopropylcarbodiimide (16.28 ml, 104 mmol) was added to the mixture. The mixture was kept at room temperature for 16 hours. The solid was removed by filtration. The filtrate was loaded on a silica gel column (silica gel 140 g), eluting with DCM. After removal of the solvent, a white solid was obtained (18.4 g, 88%).

Example 4

Synthesis of 2-(4-tritylpiperazinyl)-4,6-bis(diethanolamino)triazine (4)

Cyanuric chloride (922 mg, 5 mmol) was dissolved in a solution of THF (10 ml) containing DIEA (1.74 ml, 10 mmol). N-Tritylpiperazine (1) (1.642 g, 5 mmol) dissolved in THF (10 ml) was added to the mixture cooled in an ice bath. The mixture was kept at 0° C. and 25° C. for 30 min, respectively. Diethanolamine (5 ml, 52 mmol) was added to the mixture. The mixture was heated at 70° C. for 16 hours. The volatile materials were removed by evaporation. The residue was dissolved in EtOAc (200 ml) and washed with sodium bicarbonate (150 ml) and water (200 ml×2) and dried over sodium sulfate. After removal of the solvent, a white solid was obtained (2.82 g, 92%).

Example 5

Synthesis of 2-(4-tritylpiperazinyl)-4,6-bis[di(4-nitrophenyloxycarbonyloxyethyl)amino]triazine (5)

2-(4-Tritylpiperazinyl)-4,6-bis(diethanolamino)triazine (4) (2.82 g, 4.59 mmol) was dissolved in acetone (40 ml). TEA (1 ml) was added to the mixture, followed by bis(4-nitrophenyl) carbonate (8.4 g, 27.54 mmol). The mixture was kept at room temperature for 48 hours. The solvent was then removed. The product was obtained by column purification to give a yellowish solid.

Example 6

Synthesis of 2-(4-tritylpiperazinyl)-4,6-bis{di[di(trifluoroacetamidohexyl)aminocarbonyloxyethyl]amino}triazine (6)

2-(4-Tritylpiperazinyl)-4,6-bis[di(4-nitrophenyloxycarbonyloxyethyl)amino]triazine (5) (2.03 g, 1.6 mmol) was dissolved in acetone (40 ml). DIEA (2.8 ml, 16 mmol) was added to the mixture, followed by bis(trifluoroacetamidohexyl)amine (2) (4.16 g, 8 mmol). The reaction mixture was kept at room temperature for 16 hours. The volatile materials were removed by evaporation. The residue was chromatographed to give an oily foam (3.28 g, 87%).

Example 7

Synthesis of 2-[(4-nitrophenyl)oxycarbonylhexamethylenecarbonylpiperazinyl]-4,6-bis{di[di(trifluoroacetamidohexyl)aminocarbonyloxyethyl]amino}triazine (8)

2-(4-Tritylpiperazinyl)-4,6-bis{di[di(trifluoroacetamidohexyl)aminocarbonyloxyethyl]amino}triazine (6) (1.0 g, 0.43 mmol) was dissolved in methanol (3.2 ml) and the solution was mixed with 5% cyanoacetic acid in TFE (5 ml). The mixture was kept at room temperature for 10 min. The solvents were removed by evaporation. The residue was then diluted with DCM (50 ml) and washed with saturated sodium bicarbonate (30 ml). The organic layer was separated and dried over sodium sulfate. After removal of the solvent, the crude product 7 was dissolved in acetone (10 ml). DIEA (0.4 ml, 2.3 mmol) was added to the mixture, followed by di(4-nitrophenyl) suberate (3) (732 mg, 1.76 mmol). The reaction mixture was kept at 50° C. for 2 hours. The solvents were removed and the product was isolated from silica gel column chromatography to give an oily paste.

Example 8

General Procedure for Synthesis of a Conjugate 12 Containing the Transporter Composition and Morpholino Antisense Oligo The precursor transporter composition 8 in DMI solution containing 5% HOBT as catalyst and adequate base such as 4-methylmorpholine or triethylamine was incubated with Morpholino at 60° C. for 2 hours. After removal of the solvent, a certain volume of concentrated ammonia was added and the mixture was incubated at 50° C. for 5 hours. Same volume of 18% ammonia was added to the mixture, followed by O-methylisourea hydrochloride. The mixture was incubated at 65° C. for 45 min. Water was added to dilute the mixture and the product was isolated by using Oasis HLB LP extraction cartridge.

Example 9

Functional Quantitative Assessment of Delivery of a Conjugate Containing Transporter Composition and Morpholino in Cultured Animal Cells Details of the method were described (Summerton, J. E., U.S. Pat. No. 7,084,248). Basically, the cytosolic delivery is assessed by a quantifiable signal proportional to the amount of cargo delivered into the cytosol. This technology was developed by Kole and co-workers (Kang, S., et al. *Biochemistry* 37:6235-6239 (1998)) by using the splice-correction system, coupled with a Morpholino antisense oligo targeted against the splicing error site. A cell line has been stably transfected with a gene that codes for an RNA transcript that includes a mutation that generates a splicing error which acts to prevent the translation of luciferase coded by that RNA transcript. When a properly-targeted Morpholino antisense oligo is delivered into the cytosol/nuclear compartment of such cells, the Morpholino blocks the mutant site. This leads to normal translation of the luciferase, and the light emission from that luciferase is readily quantitated in a luminometer.

Figure 10:
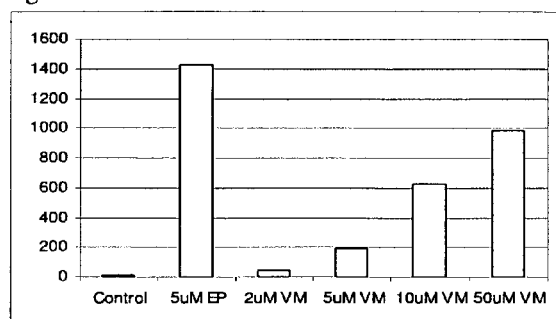
FIG. 10 illustrates the functional efficacy assay of delivering Morpholino conjugated with the transporter composition in 10% serum cell culture in comparison with the Morpholino in the presence of Endo Porter, an amphiphilic transporter peptide (Summerton, J. E. U.S. Pat. No. 7,084,248 (2006)).
Figure 10:
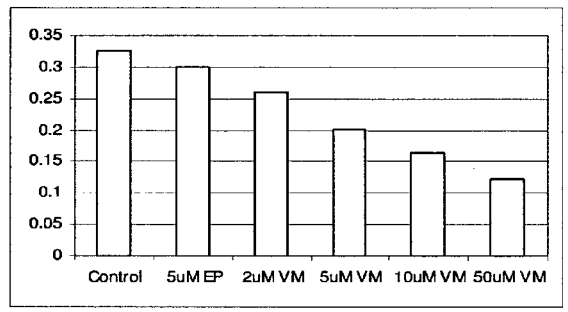
Figure 10:
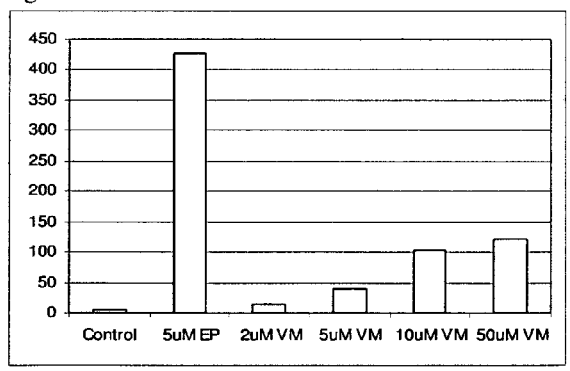

The experiments were carried out in the presence of 10% serum in comparison with Endo Porter, a peptide delivery composition (Gene Tools, LLC). After incubation at 37° C. for 24 hours, the cells are lysed and assayed for both luciferase and total cell protein. The results were shown in FIG. 10. The conjugate of transporter composition of this invention and Morpholino shows some delivery efficacy (ca. 10% compared with Endo Porter in a comparable concentration).

Alternate parallel experiments were carried out in the presence of 100% serum in comparison with Endo Porter. The results were shown in FIG. 11. The conjugate of transporter composition of this invention and Morpholino shows greater delivery efficacy (ca. 2 and 4 folds at 24 hours and 48 hours incubation, respectively, compared with Endo Porter in a comparable concentration while the higher the concentrations, the more efficient the delivery).

Example 10

Functional Quantitative Assessment of Delivery of a Conjugate Containing Transporter Composition and Morpholino In Vivo Kole and co-workers have developed a strain of transgenic mice carrying an expressed gene that codes for an RNA transcript that potentially codes for a green fluorescent protein (Sazani, P., et al. *Nature Biotechnology* 20:1228-1233 (2002)). That RNA transcript contains a mutation that causes a splicing error which prevents expression of the green fluorescent protein. Contacting an appropriate Morpholino antisense oligo with that mutant RNA transcript blocks that mutant site, thereby correcting the splicing error and generating green fluorescent protein. Thus, the technology of visualizing green fluorescence in a specific tissue has been used to assess cytosolic delivery into cells of that tissue in vivo.

The ability of the conjugate containing the transporter composition of this invention and Morpholino to achieve cytosolic delivery in vivo is assessed. The conjugate was administered intravenously at 12.5 mg/kg for 4 days into the mice of the transgenic strain and the results were shown in FIG. 12. Excellent delivery are achieved in liver, small intestine, colon, muscle and diaphragm, while fairly good in spleen and stomach, even modestly good in lung, heart, skin and brain.

The AST-ALT data was also collected (FIG. 13), indicating that the conjugate of the transporter composition of the invention and Morpholino is not toxic to the liver in mice.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A composition structured for entry into cells, which may be in a living subject, comprising:

a) a triazine ring;

b) a dendrimeric structure containing 4 to 6 guanidine groups covalently linked to a carbon of the triazine ring;

c) a dendrimeric structure containing 4 to 6 guanidine groups covalently linked to a second carbon of the triazine ring; and d) a bioactive substance covalently linked to a third carbon of the triazine ring, wherein, the composition has the structure:

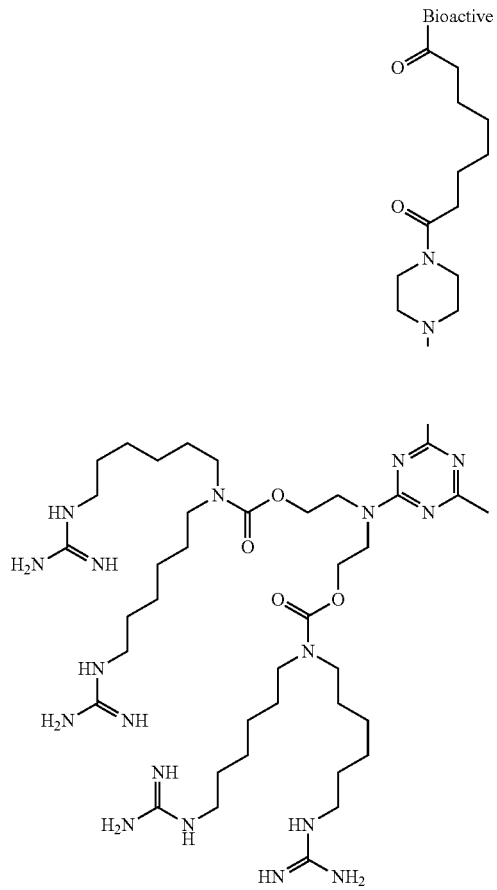

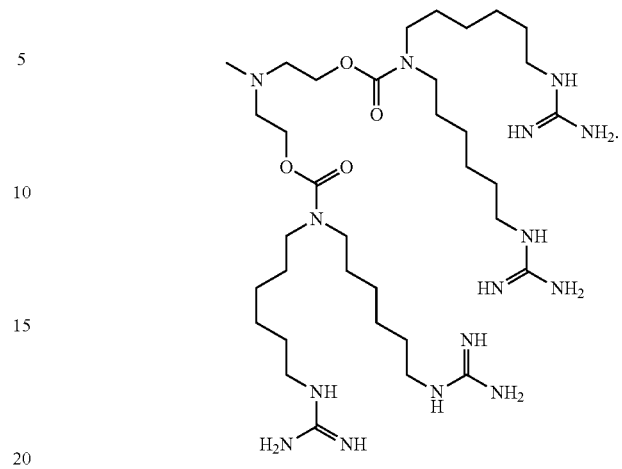

2. A composition structured for entry into cells, which may be in a living subject, comprising:

a) a triazine ring;

b) a dendrimeric structure containing 4 to 6 guanidine groups covalently linked to a carbon of the triazine ring;

c) a dendrimeric structure containing 4 to 6 guanidine groups covalently linked to a second carbon of the triazine ring; and d) a bioactive substance covalently liked to a third carbon of the triazine ring, wherein, the linkage between the triazine ring and the bioactive substance is readily cleaved within a cell and has the structure:

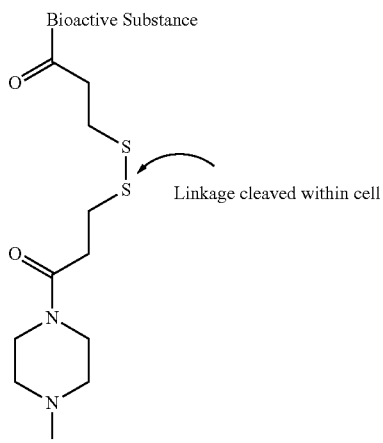

-continued

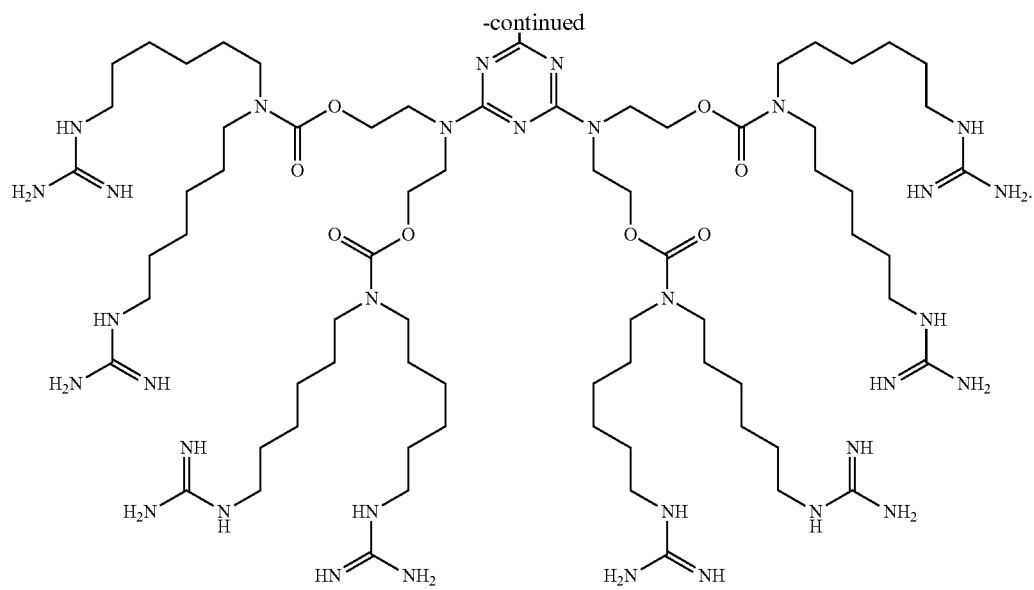

3. The composition of claim 1, wherein the bioactive substance is a Morpholino antisense oligo.

4. The composition of claim 2, wherein the bioactive substance is a Morpholino antisense oligo.

5. The composition of claim 3, wherein the Morpholino antisense oligo is effective to modify splicing of a selected mRNA.

6. The composition of claim 4, wherein the Morpholino antisense oligo is effective to modify splicing of a selected mRNA.

7. The composition of claim 5, wherein the Morpholino antisense oligo is effective to correct a splicing error in the mRNA transcript that codes for a green fluorescent protein.

* * * * *